United States Patent
Kobayashi et al.

(10) Patent No.: US 9,888,888 B2
(45) Date of Patent: Feb. 13, 2018

(54) X-RAY DIAGNOSTIC APPARATUS

(71) Applicant: Toshiba Medical Systems Corporation, Otawara-shi (JP)

(72) Inventors: Yoshimasa Kobayashi, Nasushiobara (JP); Satoru Ohishi, Otawara (JP); Shumpei Ohashi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 214 days.

(21) Appl. No.: 14/739,504

(22) Filed: Jun. 15, 2015

(65) Prior Publication Data
US 2015/0272520 A1   Oct. 1, 2015

Related U.S. Application Data

(63) Continuation of application No. PCT/JP2013/084532, filed on Dec. 24, 2013.

(30) Foreign Application Priority Data

Dec. 21, 2012 (JP) ................... 2012-279900
Dec. 24, 2013 (JP) ................... 2013-265737

(51) Int. Cl.
*A61B 6/10* (2006.01)
*A61B 6/06* (2006.01)
(Continued)

(52) U.S. Cl.
CPC ............. *A61B 6/107* (2013.01); *A61B 6/06* (2013.01); *A61B 6/4035* (2013.01); *A61B 6/487* (2013.01);
(Continued)

(58) Field of Classification Search
CPC ............ G21K 1/04; G21K 1/046; G21K 1/02; G21K 5/04
See application file for complete search history.

(56) References Cited

U.S. PATENT DOCUMENTS

2011/0013742 A1* 1/2011 Zaiki .................... A61B 6/035
378/15

FOREIGN PATENT DOCUMENTS

CN   101901485 A   12/2010
JP   01-185496 A    7/1989
(Continued)

OTHER PUBLICATIONS

International Written Opinion dated Mar. 18, 2014 in PCT/JP2013/084532 filed Dec. 24, 2013 with English translation.
International Search Report dated Mar. 18, 2014 in PCT/JP2013/084532 filed Dec. 24, 2013.
Combined Chinese Office Action and Search Report dated Mar. 28, 2017 in Patent Application No. 201380066786.0 (with English translation of Categories of Cited Documents).
(Continued)

*Primary Examiner* — Hoon Song
(74) *Attorney, Agent, or Firm* — Oblon, McClelland, Maier & Neustadt, L.L.P.

(57) ABSTRACT

According to one embodiment, an X-ray diagnostic apparatus includes an X-ray source, a plurality of lead plates, attention position specifying circuitry, stop control circuitry. The X-ray source generates X-rays. The plurality of lead plates includes an aperture which narrows an irradiation range of X-rays with which an object is irradiated by the X-ray source. The attention position specifying circuitry specifies an attention position based on a line of sight of an observer. The stop control circuitry performs movement control of the plurality of lead plates based on the specified attention position.

20 Claims, 24 Drawing Sheets

(51) Int. Cl.
    *A61B 6/00*          (2006.01)
    *H05G 1/56*          (2006.01)
    *H05G 1/60*          (2006.01)
    *G21K 1/10*          (2006.01)
    *G21K 1/04*          (2006.01)
    *H05G 1/58*          (2006.01)

(52) U.S. Cl.
    CPC ............ A61B 6/542 (2013.01); *A61B 6/4014* (2013.01); *A61B 6/4441* (2013.01); *A61B 6/461* (2013.01); *G21K 1/04* (2013.01); *G21K 1/10* (2013.01); *H05G 1/56* (2013.01); *H05G 1/58* (2013.01); *H05G 1/60* (2013.01)

(56) References Cited

FOREIGN PATENT DOCUMENTS

| | | |
|---|---|---|
| JP | 04-157400 A | 5/1992 |
| JP | 2007-159913 A | 6/2007 |
| JP | 2008-212550 A | 9/2008 |
| JP | 2008-237684 A | 10/2008 |
| JP | 2009-072360 | 4/2009 |
| JP | 2010-240254 A | 10/2010 |
| JP | 2012-075782 A | 4/2012 |

OTHER PUBLICATIONS

Japanese Office Action dated Sep. 12, 2017 in corresponding Japanese Application No. 2013-265737.

\* cited by examiner

FIG. 4A
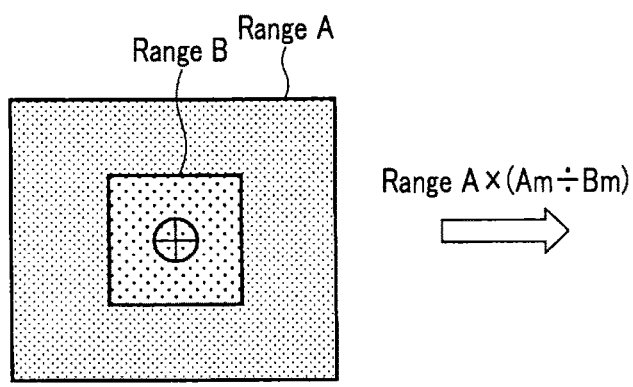
Range A × (Am ÷ Bm)
FIG. 4B
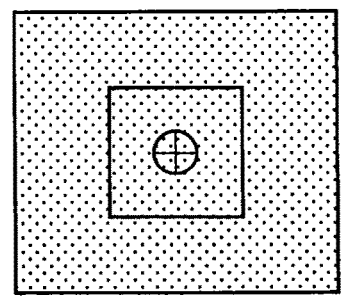
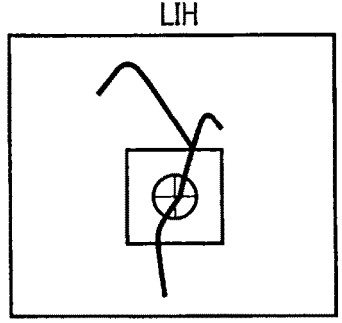
FIG. 5A
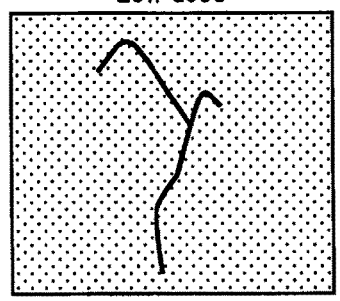
FIG. 5B
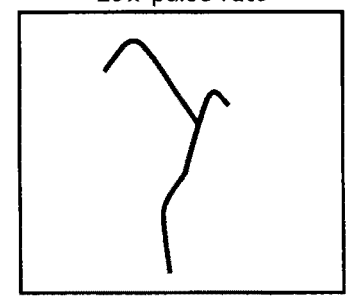
FIG. 5C

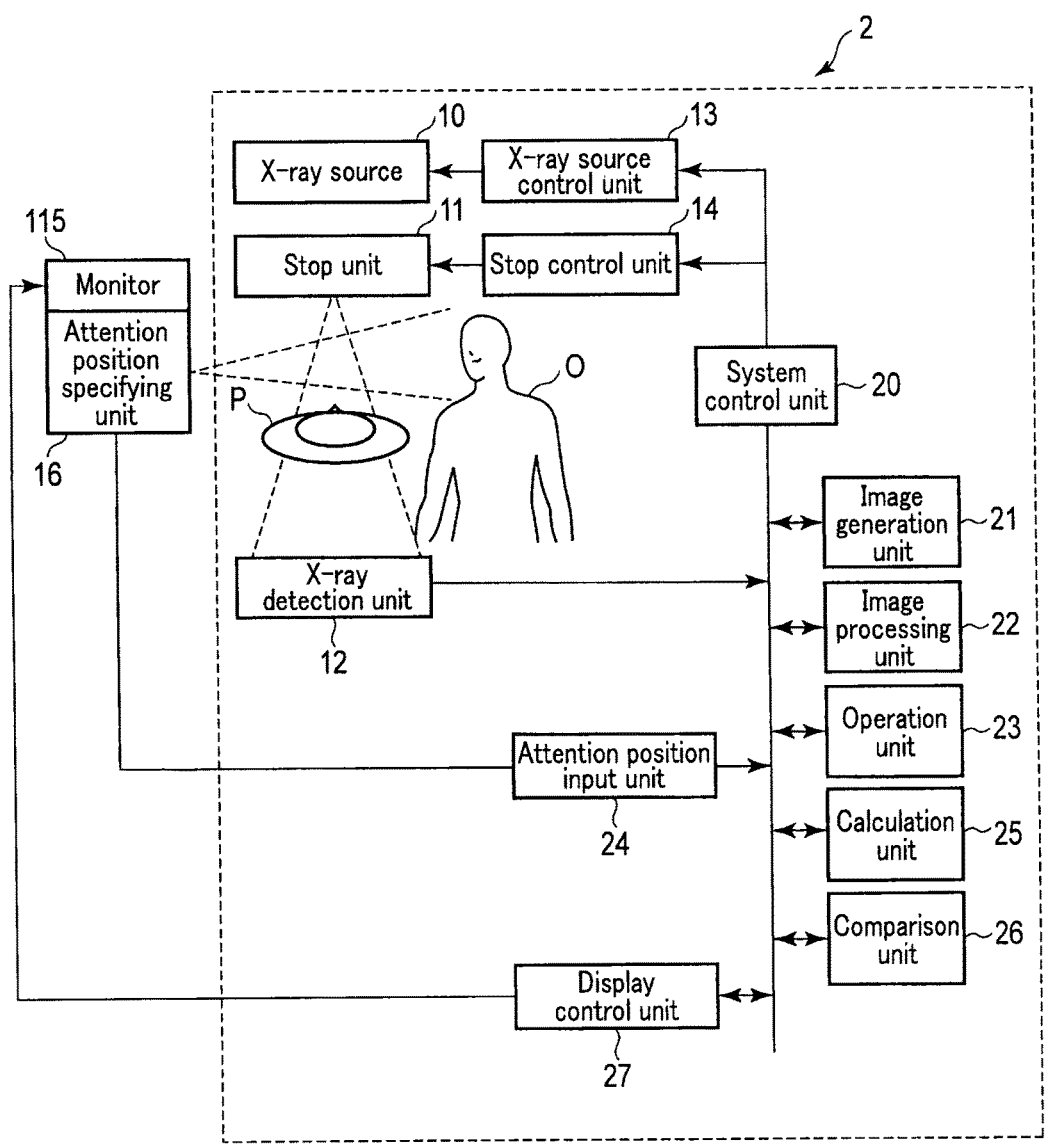
F I G. 8

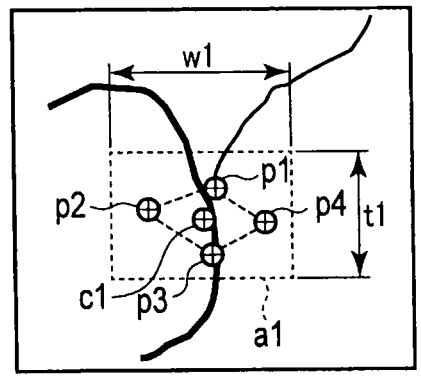
F I G. 13A
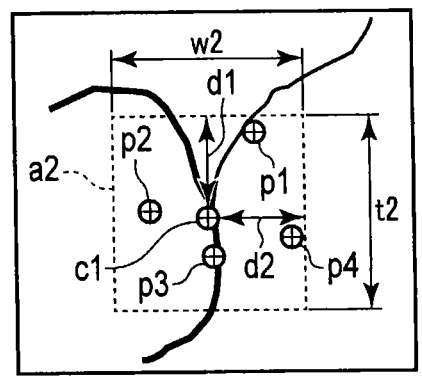
F I G. 13B

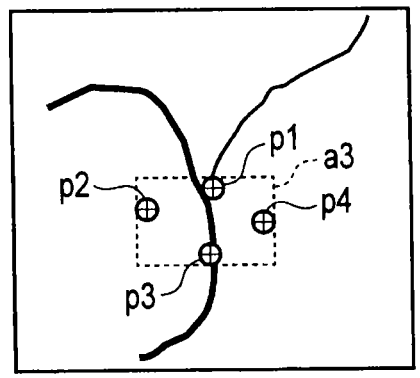
F I G. 14A
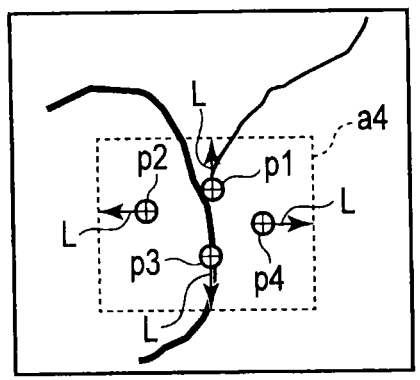
F I G. 14B

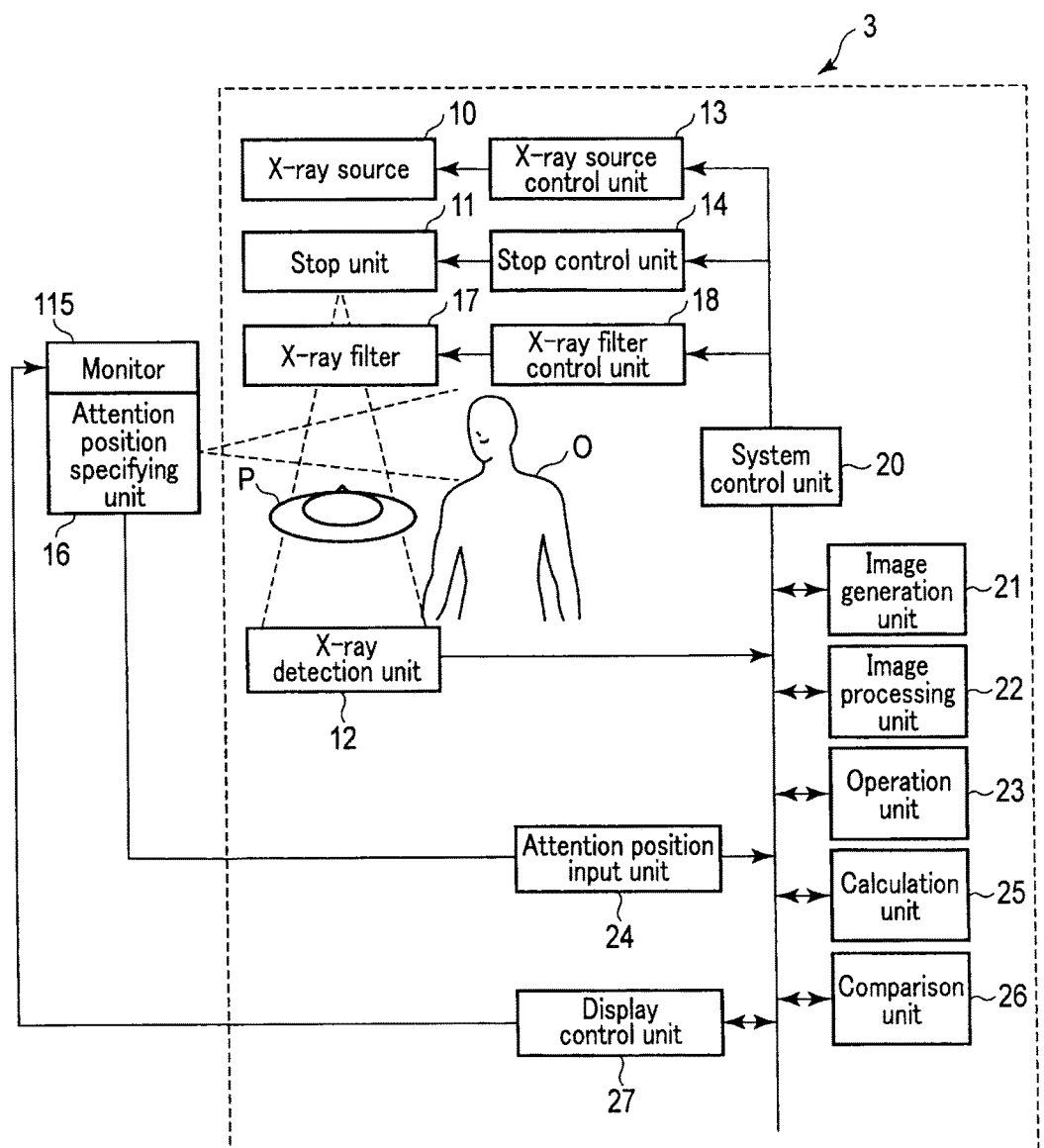
F I G. 18

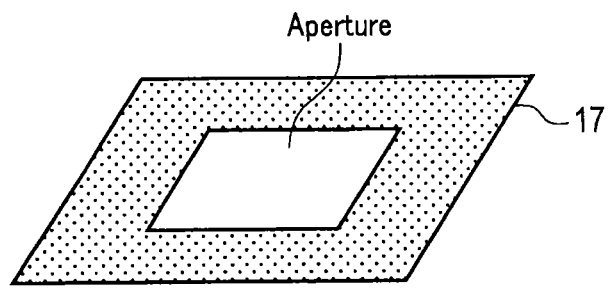
F I G. 19A
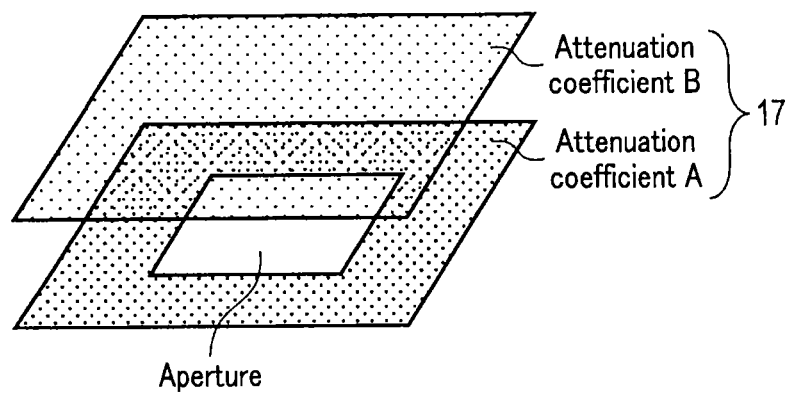
F I G. 19B
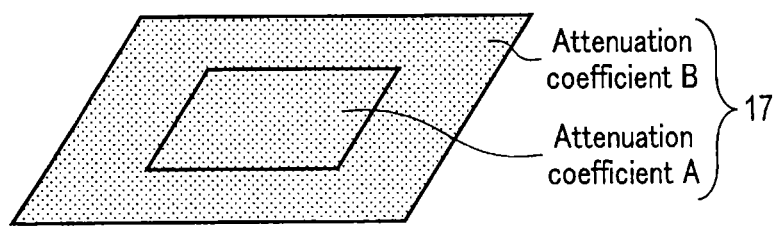
F I G. 19C

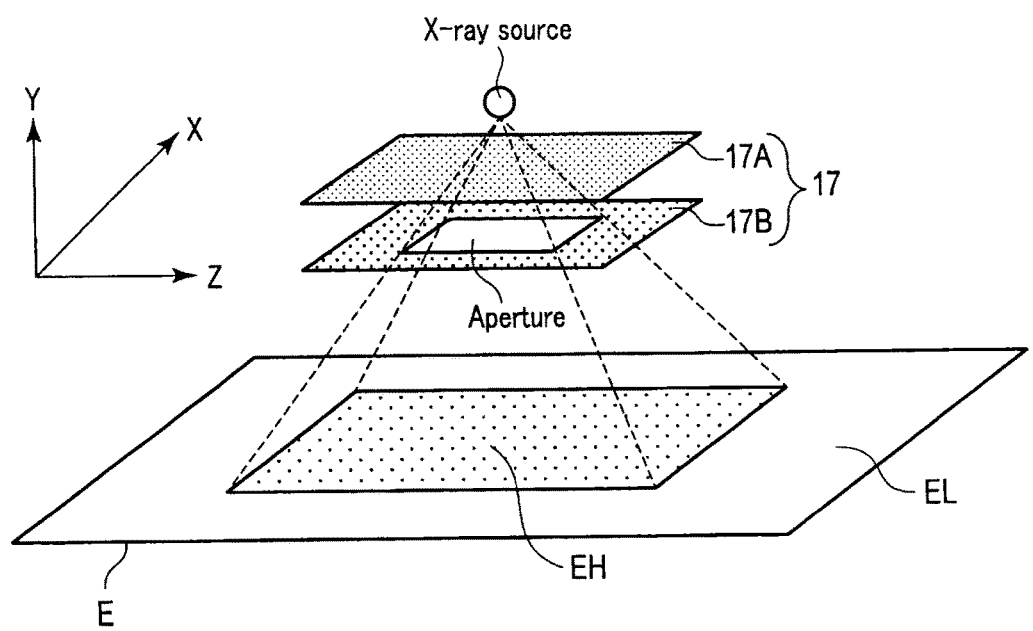
F I G. 21

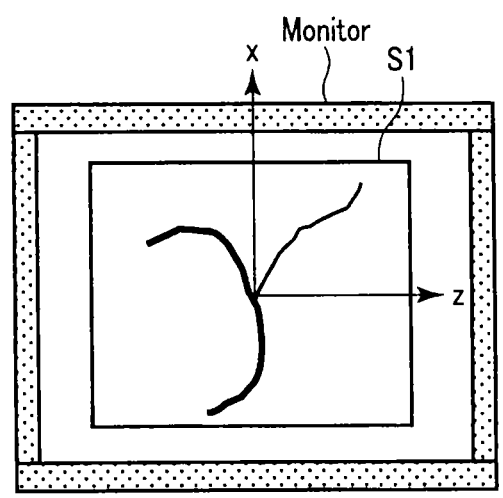
F I G. 22A
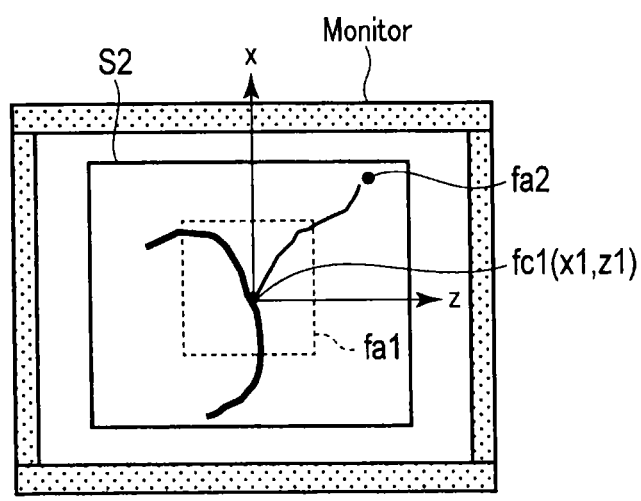
F I G. 22B

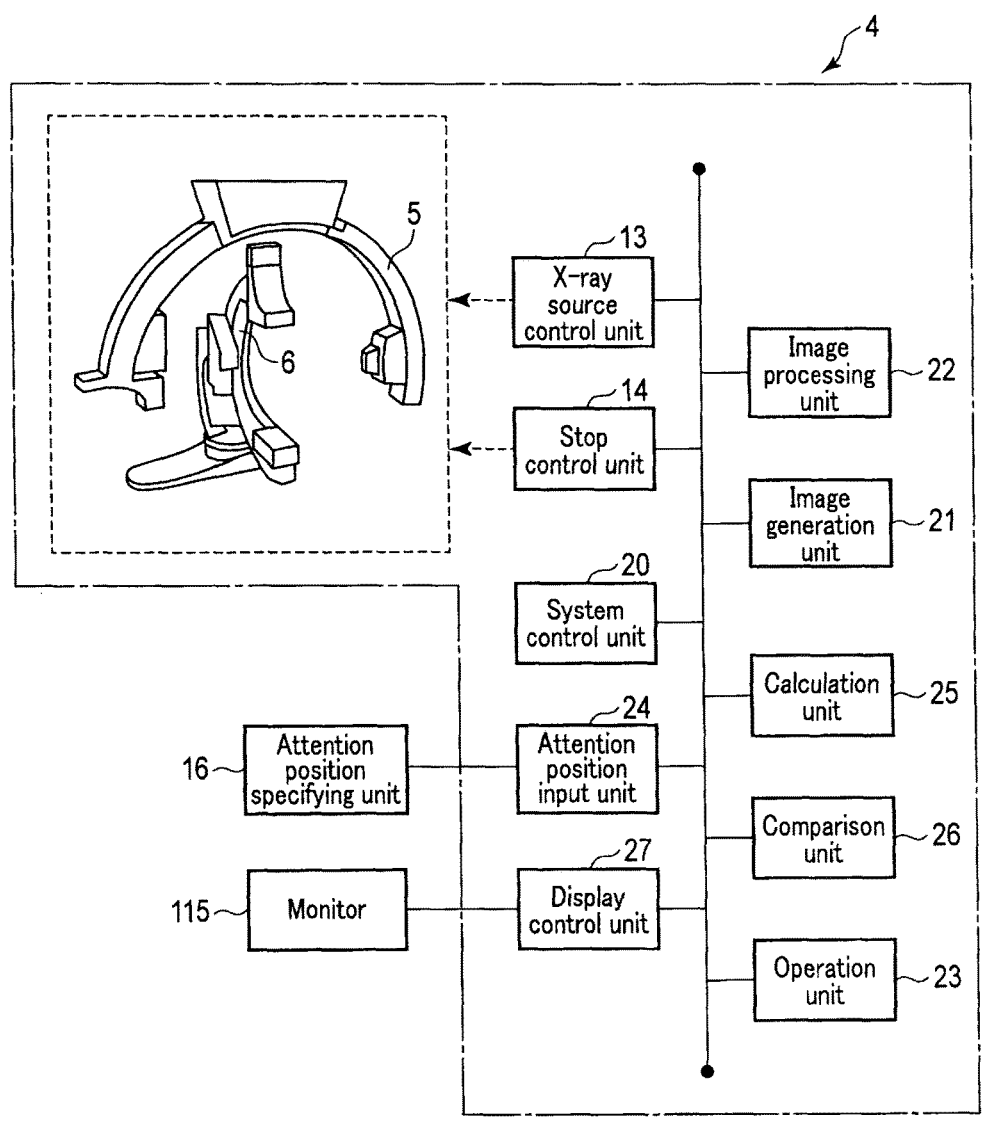
F I G. 23

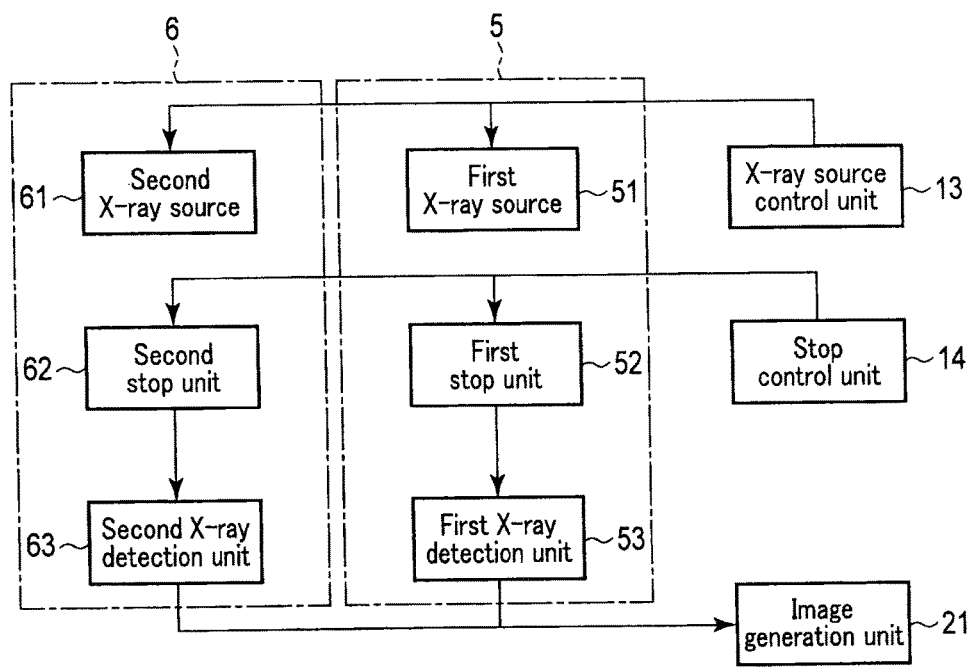
F I G. 24

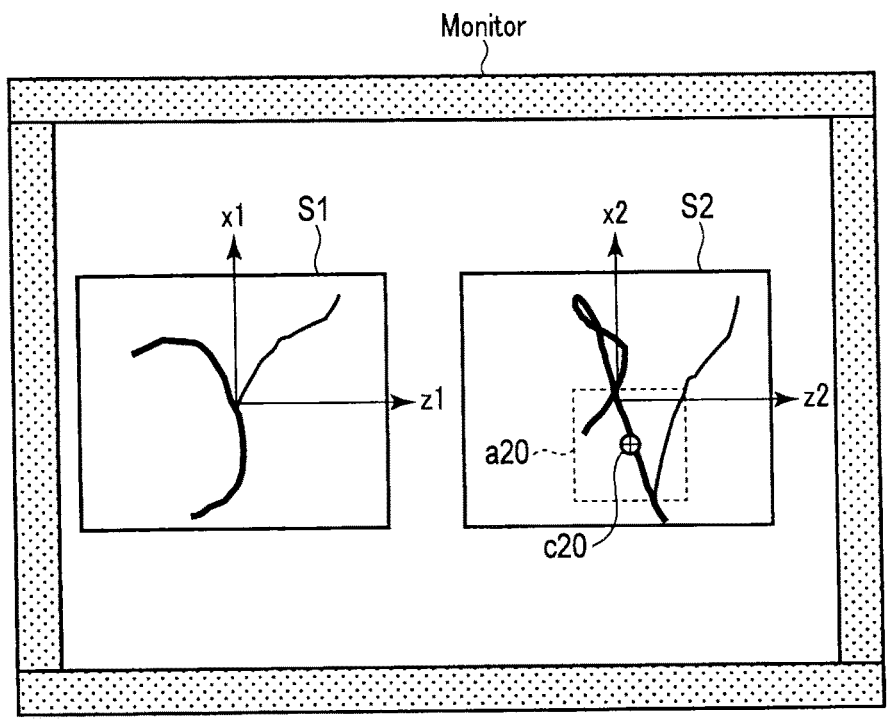
F I G. 25A
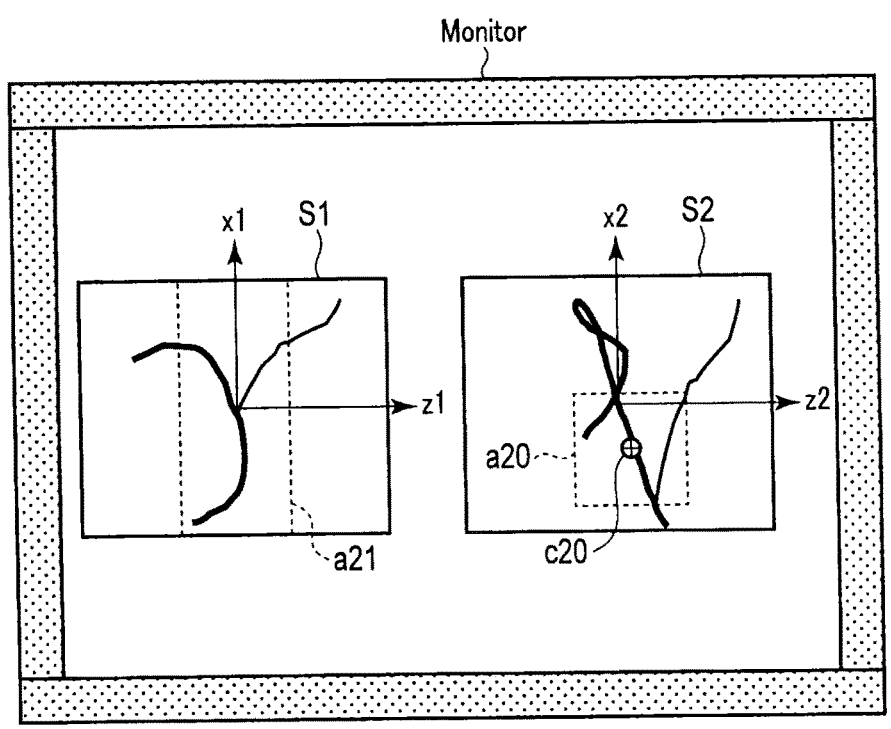
F I G. 25B

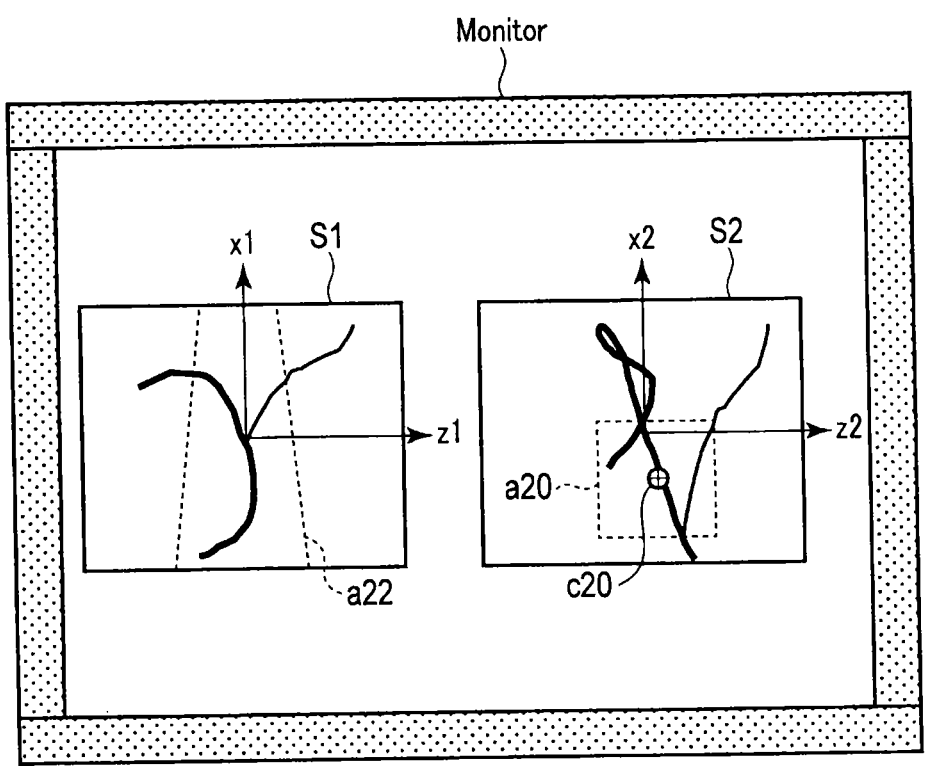
F I G. 25C

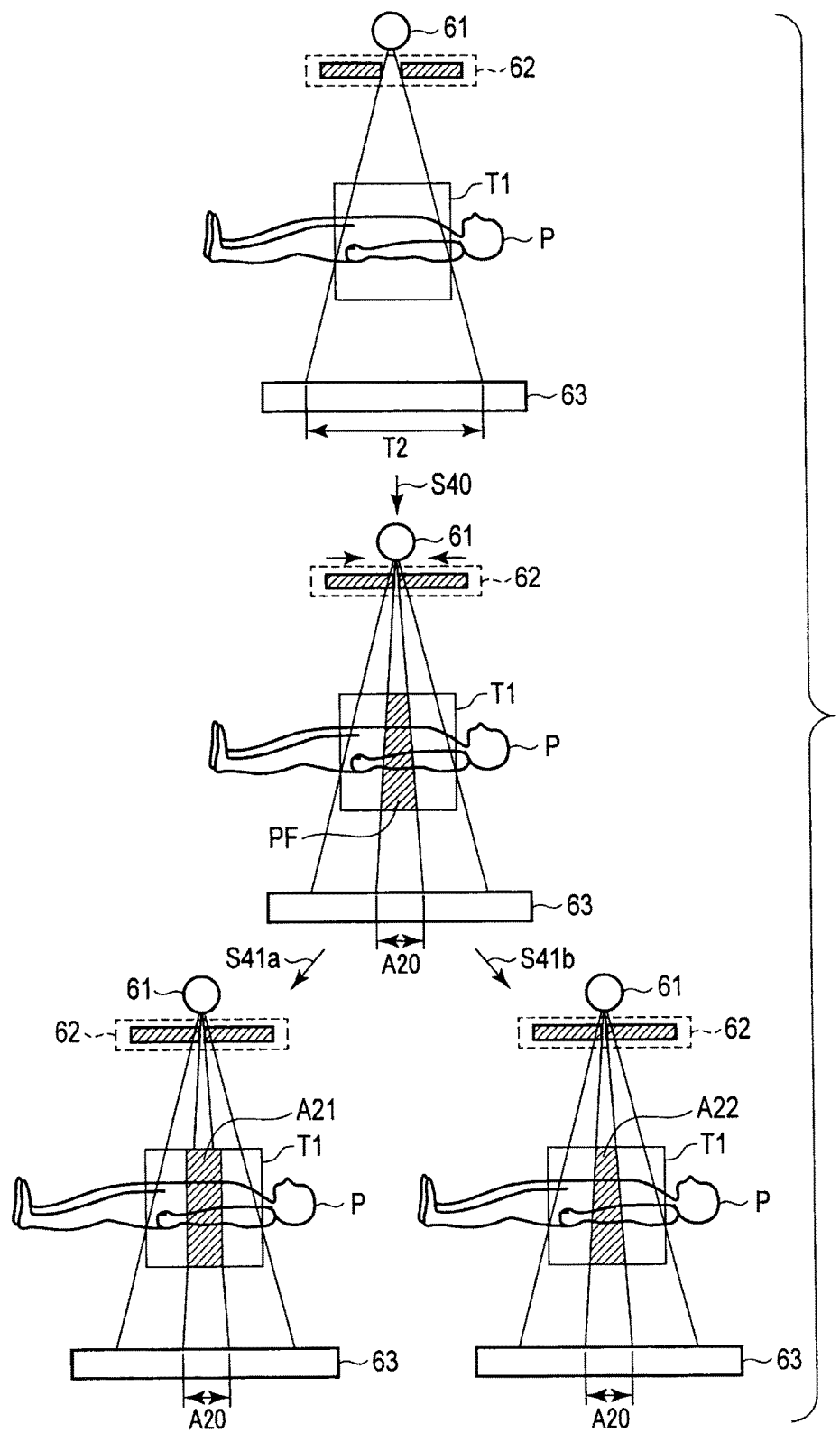
F I G. 26

X-RAY DIAGNOSTIC APPARATUS

CROSS-REFERENCE TO RELATED APPLICATIONS

This application is based upon and claims the benefit of priority from Japanese Patent Application No. 2012-279900, filed Dec. 21, 2012, Japanese Patent Application No. 2013-265737, filed Dec. 24, 2013, International Patent Application No. PCT/JP2013/084532, filed Dec. 24, 2013, the entire contents of both of which are incorporated herein by reference.

FIELD

Embodiments described herein relate generally to an X-ray diagnostic apparatus.

BACKGROUND

In diagnosis and treatment using X-rays, a technique of reducing the exposure doses of an object and operator while maintaining the qualities of the diagnosis and treatment is very important, and has been vigorously studied and developed all over the world. The merits of reducing exposure doses are to lead to the suppression of the incidence of cancer and the like and the suppression of the occurrence of cataract and the like.

For example, at the time of treatment of arrhythmia, a technique called X-ray fluoroscopy is used. X-ray fluoroscopy is a technique of continuously displaying, in real time, (moving image display) X-ray images obtained by continuously applying X-rays. The operator performs a procedure by using a device such as a catheter while checking such a moving image. In such a procedure, X-ray irradiation is sometimes continuously performed for several hours, and hence it is required to reduce the exposure doses of the object and operator in this procedure.

As a technique of suppressing exposure doses, for example, there is available a technique of performing X-ray fluoroscopy by irradiating only a region of interest (to be referred to as an ROI hereinafter) in an X-ray fluoroscopy range. In this technique, for example, the operator changes an ROI by operating a switch such as a foot switch. That is, the operator performs the above control during a procedure by some kind of operation which is not directly relevant to the procedure.

A problem to be solved by the present invention is to provide an X-ray diagnostic apparatus which reduces the exposure dose of an object without making the operator actively conscious of a reduction in exposure dose.

BRIEF DESCRIPTION OF DRAWINGS

FIG. 4A and FIG. 4B schematically show an example using a filter which attenuates X-rays as a stop unit according to the first embodiment.

FIGS. 5A-5C schematically show a display example on a display unit when the line of sight of the operator falls outside the display unit according to the first embodiment.

FIG. 8 is a schematic view showing an example of an X-ray diagnostic apparatus according to the second embodiment.

FIG. 13A is a view showing the first example of a gaze range set by the stop control unit.

FIG. 13B is a view showing the second example of a gaze range set by the stop control unit.

FIG. 14A is a view showing the third example of a gaze range set by the stop control unit.

FIG. 14B is a view showing the fourth example of a gaze range set by the stop control unit.

FIG. 18 is a schematic view showing an example of an X-ray diagnostic apparatus 3 according to the third embodiment.

FIG. 19A is view showing the first example of the X-ray filter of the X-ray diagnostic apparatus according to the third embodiment.

FIG. 19B is view showing the second example of the X-ray filter of the X-ray diagnostic apparatus according to the third embodiment.

FIG. 19C is view showing the third example of the X-ray filter of the X-ray diagnostic apparatus according to the third embodiment.

FIG. 21 is a view showing the irradiation range of X-rays generated from an X-ray source and transmitted through an X-ray filter.

FIG. 22A is a view showing an example of an X-ray image displayed on a monitor when the aperture filter of the X-ray diagnostic apparatus according to the third embodiment is not in use.

FIG. 22B is a view showing an example of an X-ray image displayed on the monitor when the aperture filter of the X-ray diagnostic apparatus according to the third embodiment is in use.

FIG. 23 is a schematic view showing an example of an X-ray diagnostic apparatus 4 according to the fourth embodiment.

FIG. 24 is a block diagram showing an example of a first imaging system 5 and a second imaging system 6.

FIG. 25A is the first view for explaining processing by a stop control unit 14 of the biplane X-ray diagnostic apparatus 4 according to the fourth embodiment.

FIG. 25B is the second view for explaining processing by the stop control unit 14 of the biplane X-ray diagnostic apparatus 4 according to the fourth embodiment.

FIG. 25C is the third view for explaining processing by the stop control unit 14 of the biplane X-ray diagnostic apparatus 4 according to the fourth embodiment.

FIG. 26 is a view for explaining a method of deciding, in accordance with a gaze range on one X-ray image, a gaze range on another X-ray image.

DETAILED DESCRIPTION

In general, according to one embodiment, an X-ray diagnostic apparatus includes an X-ray source, a plurality of lead plates, attention position specifying circuitry, stop control circuitry. The X-ray source generates X-rays. The plurality of lead plates includes an aperture which narrows an irradiation range of X-rays with which an object is irradiated by the X-ray source. The attention position specifying circuitry specifies an attention position based on a line of sight of an observer. The stop control circuitry performs movement control of the plurality of lead plates based on the specified attention position.

(First Embodiment)

The first embodiment will be described below with reference to the accompanying drawings.

Figure 1:
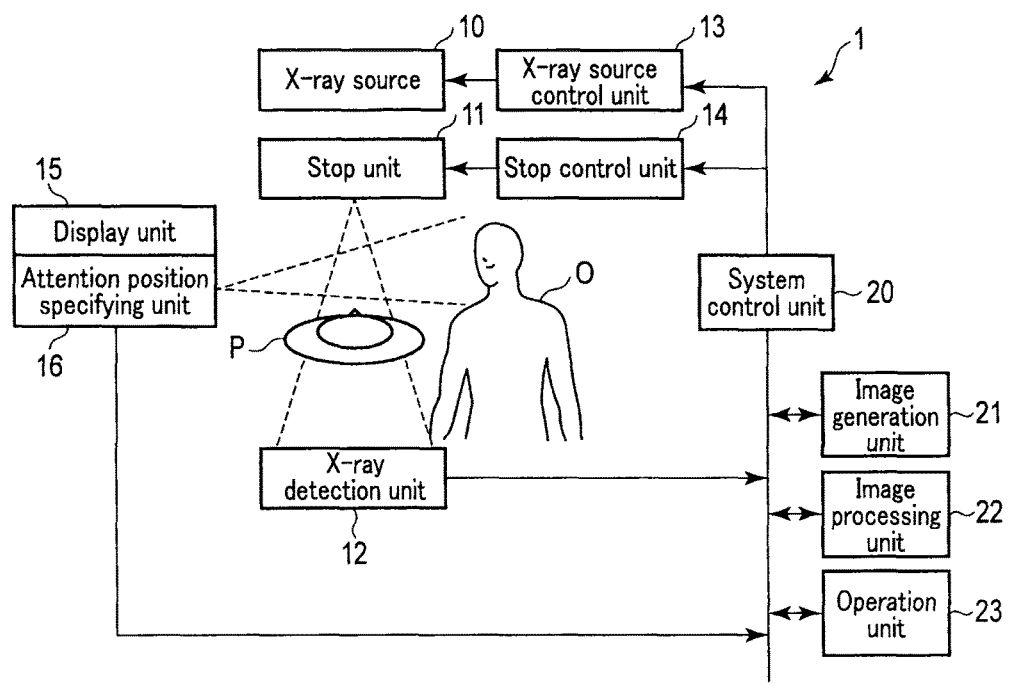
FIG. 1 is a schematic view showing an example of an X-ray diagnostic apparatus according to the first embodiment.

FIG. 1 is a schematic view showing an example of an X-ray diagnostic apparatus according to the first embodiment.

An X-ray diagnostic apparatus 1 according to the first embodiment (to be simply referred to as the X-ray diagnostic apparatus 1 hereinafter) includes an X-ray source 10 which irradiates an object P with X-rays, an X-ray detection unit (X-ray detection circuitry) 12 which detects X-rays, an X-ray source control unit (X-ray source control circuitry) 13 which controls the X-ray source 10, a stop unit 11, a stop control unit 14 (stop control circuitry) which controls the stop unit 11, a system control unit 20, an image generation unit (image generation circuitry) 21, an image processing unit 22, an operation unit (operation circuitry) 23, a display unit (display) 15, and an attention position specifying unit (attention position specifying circuitry) 16.

The X-ray source 10 includes an X-ray tube which generates X-rays upon application of a high voltage from, for example, a high voltage generation unit (not shown).

The X-ray source 10 and the X-ray detection unit 12 are held by, for example, a holding tool such as a C-arm so as to face each other.

The X-ray detection unit 12 detects the X-rays emitted from the X-ray source 10 and transmitted through the object P. The X-rays detected by the X-ray detection unit 12 are converted into a signal corresponding to the amount of X-rays.

The system control unit 20 controls the X-ray source control unit 13, the stop control unit 14, display on the display unit 15, and the like.

The stop unit 11 uses, for example, a plurality of lead plates (aperture blades) and blocks X-rays. The stop control unit 14 controls the movement of each of the plurality of lead plates of the stop unit 11. That is, the stop unit 11 is located in the irradiation range of X-rays emitted from the X-ray source 10 to limit the irradiation range of X-rays. The stop unit 11 changes the irradiation range of X-rays to be limited based on the line of sight of an operator O which is recognized by the attention position specifying unit 16. At this time, the irradiation range of X-rays limited by the stop unit 11 will be referred to as an irradiation field. In this case, the operator O is not limited to a doctor who is performing a procedure, medical treatment, or the like for the object P. For example, the operator O may be an observer such as a nurse as long as he/she is associated with a procedure, medical treatment, or the like for the object P.

The stop control unit 14 controls the operation of the stop unit 11 under the control of the system control unit 20. An operation regarding this will be described later with reference to FIGS. 3A-3D.

The X-ray source control unit 13 controls the X-ray source 10 under the control of the system control unit 20. In this case, control of the X-ray source 10 which is performed by the X-ray source control unit 13 includes, for example, control of a tube voltage value and a tube current value and control of a pulse rate.

The image generation unit 21 generates an X-ray image of the object P based on the data of the X-rays detected by the X-ray detection unit 12.

The image processing unit 22 performs image processing such as changing a window condition for the X-ray image generated by the image generation unit 21 and removal of high-frequency components.

The operation unit 23 is operated by the operator O to, for example, switch ON/OFF X-ray irradiation or switch display on the display unit 15.

The display unit 15 displays an X-ray image of the object P which is generated by the image generation unit 21. The display unit 15 then displays a moving image by continuously displaying X-ray images in real time. This moving image will be written as an X-ray fluoroscopic moving image.

The attention position specifying unit 16 includes, for example, an infrared LED and a CMOS camera, and recognizes the line of sight of the operator O who is checking the display unit 15.

The attention position specifying unit 16 irradiates the operator O with near infrared light from the infrared LED, and images corneal reflection from the eyeball of the operator O with the CMOS camera. The attention position specifying unit 16 then recognizes the line of sight by using a limbus-tracking method (scleral reflection method) of measuring eyeball movement by using, for example, the difference in reflectance between light from the sclera (white part of the eye) and light from the cornea (black part of the eye).

The attention position specifying unit 16 sends the information of the recognized line of sight such as the line-of-sight angle of the operator O to the system control unit 20. The information of the line of sight in this case is information which is obtained by measuring eyeball movement using, for example, the above limbus-tracking method and indicates the specific position of the line of sight of the operator O on the display unit 15. The position of the line of sight of the operator O is also called an attention position.

Figure 2:
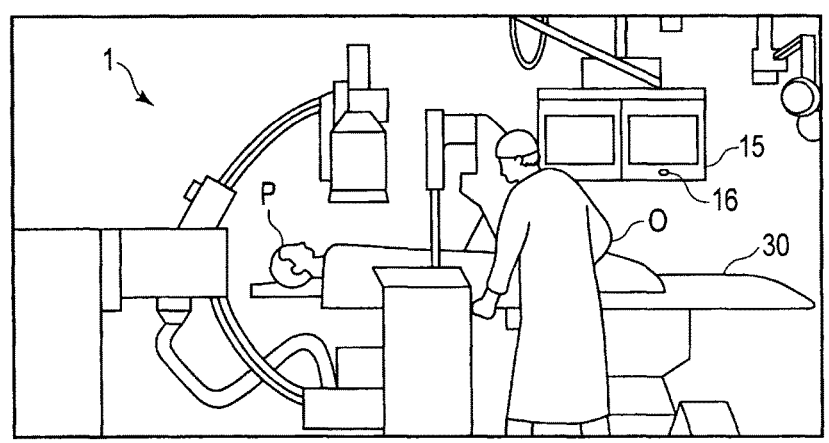
FIG. 2 is a schematic view showing a diagnosis room equipped with the X-ray diagnostic apparatus according to the first embodiment.

FIG. 2 is a schematic view showing a diagnosis room equipped with the X-ray diagnostic apparatus according to the first embodiment.

Referring to FIG. 2, the object P is placed on a bed 30, and the operator O who performs a procedure is standing next to the object P. The display unit 15 and the attention position specifying unit 16 are provided at, for example, positions at which the operator O can check the units by only slightly raising his/her head during an operation. The attention position specifying unit 16 may be incorporated in the display unit 15, attached to an upper portion of the display unit 15, or provided near the display unit 15.

FIGS. 3A-3D schematically show a method of controlling the stop unit 11 in accordance with the line of sight according to the first embodiment.

Figure 3A:
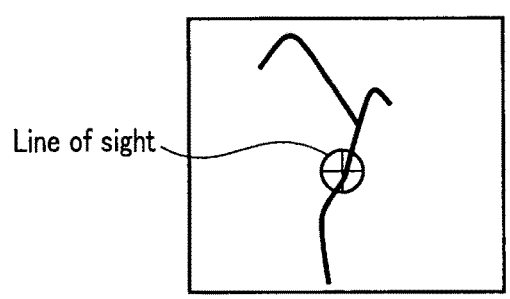
FIGS. 3A-3D schematically show a method of controlling a stop unit in accordance with the line of sight according to the first embodiment.

When, for example, performing taVI (transcatheter aortic Valve Implantation), the operator O inserts a device such as a catheter into a blood vessel while checking the run of blood vessels on the display unit 15 like that is indicated by FIG. 3A by performing X-ray fluoroscopy with respect to an object. At this time, the attention position specifying unit 16 recognizes the line of sight of the operator O who is checking the display unit 15. That is, the attention position specifying unit 16 recognizes the specific position of the line of sight of the operator O on the display unit 15. The attention position specifying unit 16 then sends the information of the recognized line of sight of the operator O to the system control unit 20.

Figure 3B:
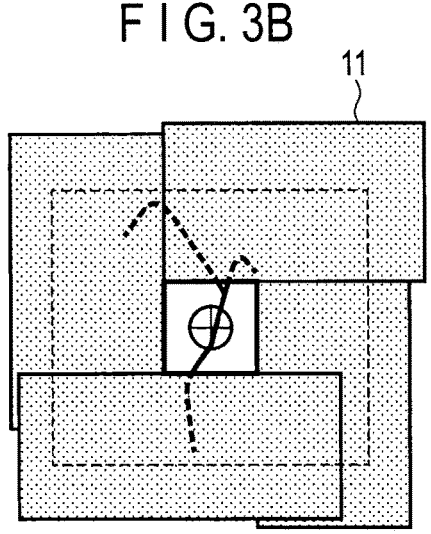

The system control unit 20 controls at least one of the X-ray source control unit 13 and the stop control unit 14 by using the information of the line of sight of the operator O recognized by the attention position specifying unit 16. For example, as indicated by FIG. 3B, the stop control unit 14 performs movement control of the stop unit 11 to change the irradiation field so as to irradiate only a range corresponding to a portion near the line of sight of the operator O with X-rays. In this case, the display unit 15 preferably displays an Last Image Hold (LIH) image in the range blocked from X-rays by the stop unit 11. The LIH image is the last image obtained when X-ray fluoroscopy is performed before X-rays are blocked by the stop unit 11. A technique concerning the LIH image is known, and hence a detailed description will be omitted.

Figure 3C:
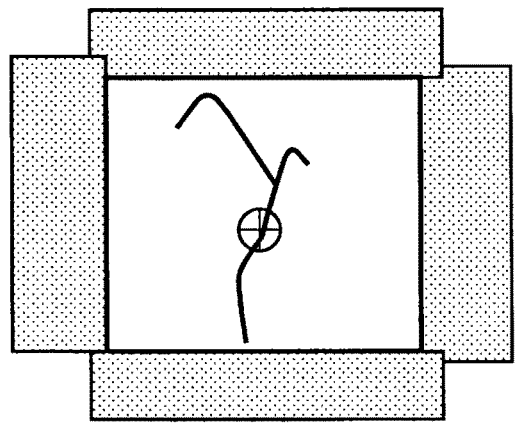

FIG. 3C indicates a schematic view showing display when the line of sight of the operator O has moved from the state indicated by FIG. 3B.

Figure 3D:
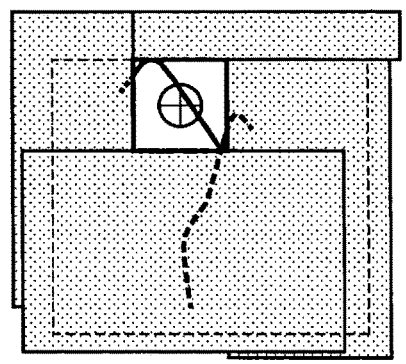

The stop control unit 14 performs movement control to retract the stop unit 11 from the X-ray irradiation range as indicated by FIG. 3C based on the movement of the line of sight (attention position) of the operator O along with the insertion of a device such as a catheter. Alternatively, the stop control unit 14 may perform movement control of the stop unit 11 to, for example, change the irradiation field by tracking a range corresponding to a portion near the line of sight of the operator O as indicated by FIG. 3D instead of retracting the stop unit 11 from the X-ray irradiation range as indicated by FIG. 3C.

It is preferable to perform movement control of the stop unit 11 based on the recognition of the line of sight of the operator O by the attention position specifying unit 16 when the line of sight of the operator O is fixed in a given region for a predetermined period of time. That is, the stop control unit 14 performs movement control of the stop unit 11 in consideration of the shift of the line of sight to some extent instead of performing movement control of the stop unit 11 only when the operator O is gazing a given pixel in a pinpoint manner. When the line of sight is fixed within a range based on the consideration of such a shift for a predetermined period of time, for example, 1 to 2 sec, the stop control unit 14 performs movement control of the stop.

Although the first embodiment has exemplified the case in which X-rays are blocked when the stop unit 11 is located in the X-ray irradiation range, this is not exhaustive. For example, as the stop unit 11, it is possible to use an X-ray filter made of aluminum or the like which attenuates X-rays. A case in which this X-ray filter is used as the stop unit 11 will be described with reference to FIG. 4A and FIG. 4B. Note that the X-ray diagnostic apparatus according to the first embodiment may include a first stop unit 11 which blocks X-rays by using, for example, lead and a second stop unit 11 which attenuates X-rays by using, for example, aluminum. In this case, it is possible to allow the operator O to select between them or to perform control in accordance with predetermined conditions such as the age of the object P.

FIG. 4A and FIG. 4B schematically show an example using an X-ray filter which attenuates X-rays as the stop unit 11 according to the first embodiment.

The stop control unit 14 performs movement control of the stop unit 11 to insert the stop unit 11 in a range corresponding to a portion near the line of sight of the operator O, as indicated by FIG. 3B, based on the recognition of the line of sight of the operator O by the attention position specifying unit 16. At this time, the stop unit 11 attenuates X-rays instead of completely blocking X-rays. Therefore, the display unit 15 displays an X-ray fluoroscopic moving image in real time even in the range input by the stop unit 11.

Note that, because of the difference between the doses of X-rays applied, an X-ray image (to be referred to as an X-ray image a hereinafter) in an X-ray fluoroscopic moving image (to be referred to as an X-ray fluoroscopic moving image a hereinafter) in a range a in which the stop unit 11 is inserted differs in image level from an X-ray image (to be referred to an X-ray image B hereinafter) in an X-ray fluoroscopic moving image (to be referred to as an X-ray fluoroscopic moving image B hereinafter) in a range B in which the stop unit 11 is not inserted (FIG. 4A). That is, the X-ray image a differs in image level from the X-ray image B because of the difference between the electrical signals converted by the X-ray detection unit 12 with and without the insertion of the stop unit 11.

Under the circumstance, the image processing unit 22 may perform processing for matching the image level of the X-ray image a with that of the X-ray image B. For example, the image processing unit 22 removes high-frequency components from the X-ray image a and the X-ray image B to generate an X-ray image a' and an X-ray image B' of low-frequency components. The image processing unit 22 then calculates an average value am of image levels in the range a and an average value Bm of image levels in the range B, and multiplies the image level of the X-ray image B' by the value of Am÷Bm. With this operation, the display unit 15 displays an X-ray fluoroscopic moving image without brightness unevenness between the range A and the range B (in FIG. 4B).

Note that an image level in this case indicates, for example, the luminance of pixels constituting an image.

A case in which the operator O has moved the line of sight outside the display unit 15 will be described next.

FIGS. 5A-5C schematically show a display example on the display unit 15 when the line of sight of the operator O falls outside the display unit 15.

Based on a situation in which the attention position specifying unit 16 recognizes that the line of sight of the operator O falls outside the display unit 15, the system control unit 20 may perform, for example, various types of control as follows:

(1) causing the stop control unit 14 to perform movement control of the stop unit 11 so as to cover the entire X-ray irradiation range, i.e., causing the display unit 15 to display an LIH image in the entire display region (in FIG. 5A);

(2) causing the X-ray source control unit 13 to perform control to, for example, decrease the tube current value and reduce the X-ray irradiation dose, i.e., causing the display unit 15 to display a noisy X-ray fluoroscopic moving image at a low dose (in FIG. 5B); and (3) causing the X-ray source control unit 13 to perform control to, for example, decrease the pulse rate and reduce the X-ray irradiation dose, i.e., causing the display unit 15 to display a moving image which is displayed with a low frequency of update and hence is not very smooth (in FIG. 5C).

It is possible to independently or simultaneously perform (2) and (3). The operator O may make settings, in advance at an arbitrary timing, as to how to use, for example, these three control methods. Alternatively, the system control unit 20 may perform these control methods stepwise. When performing the methods stepwise, the system control unit 20 performs control described in (1) if the line of sight of the operator O falls outside the display unit 15 at given time t. If the line of sight of the operator O keeps falling outside the display unit 15 until time t' after time t, the system control unit 20 performs control described in (2) and (3).

An example of performing operator identification in addition to line-of-sight recognition will be described next.

Figure 6:
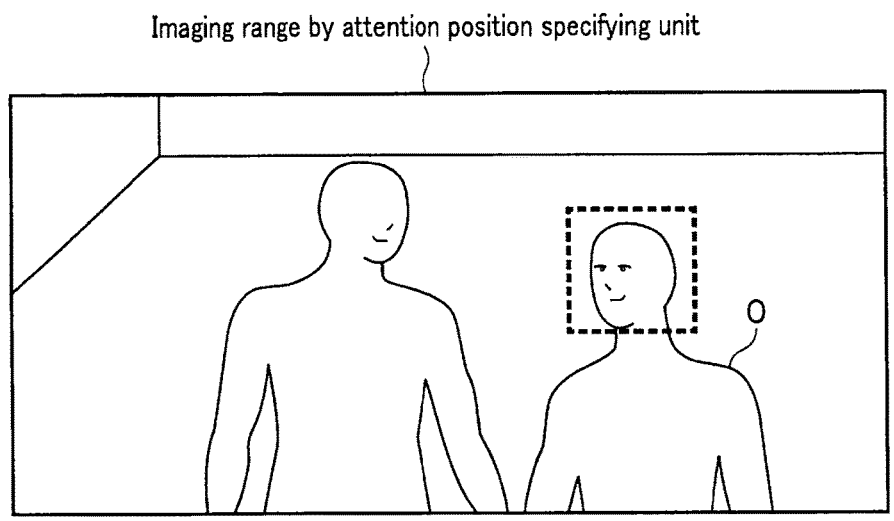
FIG. 6 is a schematic view showing an example in which two persons exist in the imaging range of a camera as an attention position specifying unit according to the first embodiment.

FIG. 6 is a schematic view showing an example in which two persons exist in the imaging range of the camera which is the attention position specifying unit 16.

The attention position specifying unit 16 identifies one of the persons as the operator O and recognizes only the line of sight of the operator O. In this case, for example, the attention position specifying unit 16 recognizes the operator O by the following methods.

(1) The face of the operator O stored in advance is matched with the faces of persons existing in the imaging range of the camera provided in the attention position specifying unit 16.

The attention position specifying unit 16 detects the face of the operator O stored in advance in a storage unit (not shown) by using a face detection technique (the dotted rectangle in FIG. 6). The attention position specifying unit 16 then recognizes the line of sight of the operator O.

(2) A specific operation stored in advance which is performed by the operator O is detected.

The attention position specifying unit 16 detects, for example, a peace sign. The attention position specifying unit 16 recognizes the line of sight of a person (operator) who has made a peace sign.

Although the first embodiment has exemplified the case in which various types of control are performed by using the line of sight of the operator O, these control operations may be performed in coordination with the operation of the operation unit 23 such as a foot switch as in the related art. When the operator O operates the operation unit 23 such as a foot switch, the function for each type of control may be switched ON/OFF by using the line of sight of the operator O.

Figures 7A, 7B:
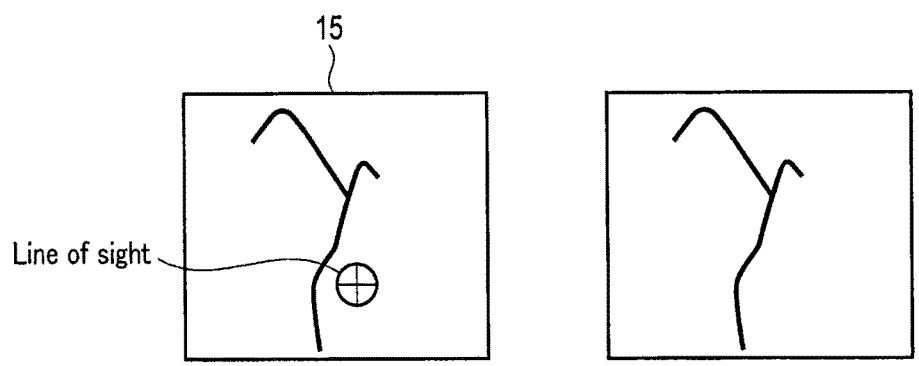
FIG. 7A and FIG. 7B schematically show the line of sight of the operator according to the first embodiment.

Note that "a state in which the line of sight falls within the display unit 15" in the first embodiment is a state in which the operator O is casting his/her line of sight into the range of the display unit 15 as indicated by FIG. 7A. In contrast to this, "a state in which the line of sight falls outside the display unit 15" is a state in which the operator O is casting his/her line of sight outside the range of the display unit 15, as indicated by FIG. 7B.

Although the single-plane X-ray diagnostic apparatus including one each of the X-ray source 10 and the X-ray detection unit 12 has been described, it is not exhaustive. For example, the first embodiment can be applied to even a biplane X-ray diagnostic apparatus including two sets of X-ray sources 10 and X-ray detection units 12.

An example of the first embodiment of a biplane X-ray diagnostic apparatus will be described below.

In the biplane X-ray diagnostic apparatus, the display unit 15 displays two types of X-ray fluoroscopic moving images based on the X-rays obtained from the respective X-ray detection units 12. In this case, for example, the apparatus may include two display units 15 or may display two X-ray fluoroscopic moving images in the segmented regions in one display unit 15.

The operator O checks one of two types of displayed X-ray fluoroscopic moving images during a procedure. Alternatively, the operator O may also cast his/her line of sight onto, for example, the object P instead of the display unit 15 without checking any of the X-ray fluoroscopic moving images. In any case, the operator O does not often simultaneously cast his/her line of sight onto the two types of displayed X-ray fluoroscopic moving images.

The system control unit 20 therefore controls at least one of the X-ray source control unit 13 and the stop control unit 14 by using the information of the line of sight of the operator O recognized by the attention position specifying unit 16. For example, the system control unit 20 changes X-ray conditions on the X-ray source 10 for generating an X-ray fluoroscopic moving image which is not checked by the operator O. To change X-ray conditions in this case is to change at least one of conditions including a tube voltage, a tube current, and a pulse rate. That is, at this time, the dose of X-rays emitted from the X-ray source 10 for the generation of an X-ray fluoroscopic moving image onto which the line of sight of the operator O is not cast is reduced as compared with the dose of X-rays emitted from the X-ray source 10 for the generation of an X-ray fluoroscopic moving image onto which the line of sight of the operator O is cast.

On the other hand, for example, the system control unit 20 controls the stop control unit 14 to move the stop unit 11 into the irradiation range of X-rays emitted from the X-ray source 10 for the generation of an X-ray fluoroscopic moving image which is not checked by the operator O. This will prevent the object P from being irradiated with X-rays in the range covered by the stop unit 11 when lead is used for the stop unit 11. Alternatively, when an X-ray filter made of aluminum or the like is used as the stop unit 11, the dose of X-rays applied to the object P is reduced by making the X-ray filter attenuate X-rays.

Although the first embodiment has exemplified the case in which an X-ray fluoroscopic moving image is displayed fully in the display unit 15, the X-ray fluoroscopic moving image may be displayed in a given region segmented in the display unit 15.

The effects of the first embodiment will be described below.

According to the first embodiment, the X-ray source control unit 13 (/the stop control unit 14) controls the X-ray irradiation dose (/controls the movement of the stop unit 11) based on the position of the line of sight of the operator which is recognized by the attention position specifying unit. This makes it possible to reduce the X-ray exposure dose of the object in a range other than the irradiation field corresponding to a portion near the point onto which the operator is casting his/her line of sight during a procedure. That is, the operator can reduce the exposure while concentrating on a procedure without being actively conscious of a reduction in exposure during the procedure.

In addition, using an X-ray filter for attenuating X-rays as the stop unit 11 allows the display unit to display an X-ray fluoroscopic moving image even outside a range corresponding to a portion near the point onto which the operator is casting his/her line of sight. This allows the operator to perform a procedure while checking a state in a range outside the irradiation field in real time and reducing the exposure.

In addition, it is possible to reduce unnecessary exposure on an object by changing X-ray conditions for the X-ray source 10 for the generation of an X-ray fluoroscopic moving image to which the line of sight of the operator is not cast. This will also contribute to a reduction in power consumption.

(Second Embodiment)

An X-ray diagnostic apparatus according to the second embodiment will be described below.

FIG. 8 is a schematic view showing an example of an X-ray diagnostic apparatus 2 according to the second embodiment.

The X-ray diagnostic apparatus 2 according to the second embodiment (to be simply referred to as the X-ray diagnostic apparatus 2 hereinafter) includes an X-ray source 10, an X-ray detection unit 12, an X-ray source control unit 13, a stop unit 11, a stop control unit 14, a system control unit 20, an image generation unit 21, an image processing unit 22, an operation unit 23, a display control unit 27, an attention position input unit 24, a calculation unit (calculation circuitry) 25, and a comparison unit (comparison circuitry) 26.

The X-ray source 10 generates X-rays from a focus upon receiving a high voltage (tube voltage) and a tube current from a high voltage generation unit (not shown). The generated X-rays exit from the radiation window of the X-ray source 10, pass through an X-ray filter (not shown) and the stop unit 11, and is applied to an object P by the operator. The X-ray source control unit 13 controls the high voltage generation unit under the control of the system control unit 20. The X-ray source control unit 13 controls a tube voltage value and a tube current value to be applied to the X-ray source 10. The X-ray source control unit 13 also controls the timing at which a tube voltage and a tube current are applied to the X-ray source 10, i.e., a pulse rate.

The stop unit 11 has aperture blades which narrow the irradiation range of X-rays exiting from the radiation window of the X-ray source 10. The stop unit 11 has, for example, a plurality of aperture blades to form an aperture. The aperture blades are moved under the control of the stop control unit 14. This changes the size and position of the aperture of the stop unit 11. The stop control unit 14 will be described in detail later.

The X-ray irradiation system constituted by the X-ray source 10 and the stop unit 11 is held on, for example, one end of a C-arm (not shown). The X-ray detection unit 12 is held on the other end of the C-arm so as to face the X-ray irradiation system.

The X-ray detection unit 12 is held on, for example, one end of the C-arm (not shown). The X-ray detection unit 12 includes a plurality of X-ray detection elements. The plurality of X-ray detection elements are arranged in a two-dimensional array. The detector in the two-dimensional array is called an Flat Panel Display (FPD). Each element of the FPD detects the X-rays emitting from the X-ray irradiation system and transmitted through the object P. Each element of the FPD outputs an electrical signal corresponding to the intensity of detected X-rays.

The image generation unit 21 generates the data of an X-ray image concerning the object P based on an output from the X-ray detection unit 12. The pixel value assigned to each pixel constituting an X-ray image is a value corresponding to an X-ray attenuation coefficient concerning a material on the transmission path of X-rays.

The image processing unit 22 executes image processing for the data of the X-ray image generated by the image generation unit 21. The image processing includes, for example, changing window conditions and removal of high-frequency components.

The display control unit 27 outputs the data of the X-ray image of the object P generated by the image generation unit 21 to an external monitor 115. The external monitor 115 displays an X-ray image of the object P in accordance with an output from the display control unit 27. More specifically, the display control unit 27 outputs the data of a plurality of X-ray images constituting the time-series data generated by the image generation unit 21 to the external monitor 115. The external monitor 115 continuously receives X-ray images concerning the object P from the display control unit 27 and displays them as an X-ray fluoroscopic moving image. In positive beam limitation processing to be described later, the display control unit 27 matches the anatomical position of a fluoroscopic moving image corresponding to the aperture of the stop unit 11 (corresponding to the gaze range of the operator O on the monitor 115) onto an LIH image, and displays the resultant image on the monitor 115. The LIH image is an X-ray image corresponding to the aperture before it is subjected to positive beam limitation, and an image immediately before the aperture is subjected to positive beam limitation. Note that like the X-ray diagnostic apparatus 1 according to the first embodiment, the X-ray diagnostic apparatus 2 may include, as its constituent element, the monitor 115 which displays the X-ray image generated by the image generation unit 21.

The operation unit 23 functions as an interface for inputting instruction information from an operator O to the X-ray diagnostic apparatus 2 according to the second embodiment. The instruction information includes, for example, an instruction to set X-ray conditions and an instruction to set an imaging direction. The operation unit 23 includes, for example, an operation console for moving the c-arm including the X-ray source 10 and the X-ray detection unit 12 in accordance with an imaging operation. The operation console includes buttons, a handle, and a trackball. The user can move the C-arm to a desired imaging position by operating the operation console. In addition, the operation unit 23 may include switches for turning ON/OFF an positive beam limitation function, an automatic tracking function, and an automatic enlargement function (all of which will be described later). The switch is preferably as a foot switch.

The attention position input unit 24 repeatedly receives information concerning the attention position of the operator O on the monitor 115 which is output from an external attention position specifying unit 16. Information concerning the attention position of the operator O on the monitor 115 is the coordinate information of the attention position (to be referred to as the monitor attention position hereinafter) in a two-dimensional coordinate system (to be referred to as a monitor 115 coordinate system hereinafter) on the image display screen of the monitor 115 as a plane.

The external attention position specifying unit 16 includes a device for specifying an attention position. The device includes, for example, an infrared LED and a CMOS camera. These devices are mounted on, for example, the upper portion of the monitor. The attention position specifying unit 16 specifies the monitor attention position of the operator O by the limbus-tracking method (scleral reflection method) using these devices. More specifically, the attention position specifying unit 16 specifies the central position of the pupil of the operator O based on the image obtained by the CMOS camera. In addition, the infrared LED irradiates the operator O with near infrared light. The attention position specifying unit 16 then specifies the position of reflection on the eyeball surface (cornea) based on the image obtained by the CMOS camera. The central position of the pupil is influenced by the movement of the line of sight of the operator O. In contrast to this, the position of cornea reflection is not influenced by the movement of the line of sight of the operator O. For this reason, the attention position specifying unit 16 can specify the line of sight of the operator O (line-of-sight angle) based on the central position of the pupil and the position of cornea reflection. The position and line-of-sight angle of the operator O are expressed by the coordinate system of the CMOS camera. For this reason, matching the coordinate system of the CMOS camera to that of the monitor 115 can specify the monitor attention position of the operator O. The coordinate system of the CMOS camera can be matched to that of the monitor 115 by, for example, registering the mounting positions of the CMOS camera and infrared LED with respect to the monitor 115 in the X-ray diagnostic apparatus 2. In addition, the coordinate system of the CMOS camera may be matched to that of the monitor 115 by executing calibration for matching between the position of the CMOS camera, the position of the infrared LED, and the position of the monitor 115 before an examination. This calibration allows the operator O to input his/her attention position onto the monitor 115 via the operation unit 23 while these devices are operating. The attention position specifying unit 16 repeatedly specifies the monitor attention position of the operator O in a predetermined cycle, and outputs the position information to the attention position input unit 24. That is, the attention position input unit 24 receives the data of a plurality of monitor attention positions constituting time-series data. Note that like the X-ray diagnostic apparatus 1 according to the first embodiment, the X-ray diagnostic apparatus 2 may include the attention position specifying unit 16 as a constituent element. In addition, the attention position specifying unit 16 may output data concerning the line of sight (line-of-sight angle) of the operator O and the data of the distance of the operator O with respect to the monitor 115 to the attention position input unit 24. The distance of the operator O with respect to the monitor 115 can be specified based on the time when the infrared LED emits infrared light and the time when the infrared light reflected by the object P is received. At this time, the calculation unit 25 may calculate the monitor attention position of the operator O based on the line of sight of the operator O, the distance of the operator O with respect to the monitor 115, and the position of the monitor 115.

The stop control unit 14 converts the monitor attention position expressed by the coordinate system of the monitor 115 into an attention position (to be referred to as an image attention position hereinafter) in the coordinate system of the X-ray image (to be simply referred to as the image coordinate system hereinafter) displayed on the monitor 115. The attention position input unit 24 repeatedly receives the data of monitor attention positions from the attention position specifying unit 16 in a specific cycle. The stop control unit 14 converts a plurality of monitor attention positions constituting time-series data into a plurality of corresponding image attention positions, respectively. In addition, the stop control unit 14 decides the size and central position of the aperture of the stop unit 11 based on a plurality of image attention positions constituting time-series data. The stop control unit 14 then controls the stop unit 11 in accordance with the decided size and central position of the aperture. The stop control unit 14 will be described in detail later.

The calculation unit 25 specifies a movement amount between two image attention positions. The calculation unit 25 calculates the total movement amount of a predetermined number of consecutive image attention positions of the plurality of image attention positions constituting time-series data. The predetermined number indicates, in the comparison unit 26 (to be described later), the number of image attention positions for determination whether the operator O is gazing. Therefore, the predetermined number may be designated by a time. In this case, the calculation unit 25 calculates the total movement amount of a plurality of image attention positions within a predetermined time.

The comparison unit 26 compares the total movement amount data output from the calculation unit 25 with a threshold in positive beam limitation processing. If the comparison result indicates that the total movement amount is less than the threshold, the comparison unit 26 determines that the operator O is gazing. If the total movement amount is equal to or more than the threshold, the comparison unit 26 determines that the operator O is not gazing.

The system control unit 20 receives information input to the X-ray diagnostic apparatus 2, and temporarily stores the input information in a memory circuit. The system control unit 20 then controls the respective units of the X-ray diagnostic apparatus 2 based on this input information.

(Positive Beam Limitation Function)

The positive beam limitation function is a function of performing positive beam limitation of the aperture of the stop unit 11 and moving the central position of the aperture in accordance with the image attention position of the operator O on the X-ray image displayed on the monitor 115. Processing concerning the positive beam limitation function (positive beam limitation processing) will be described with reference to FIG. 9.

Figure 9:
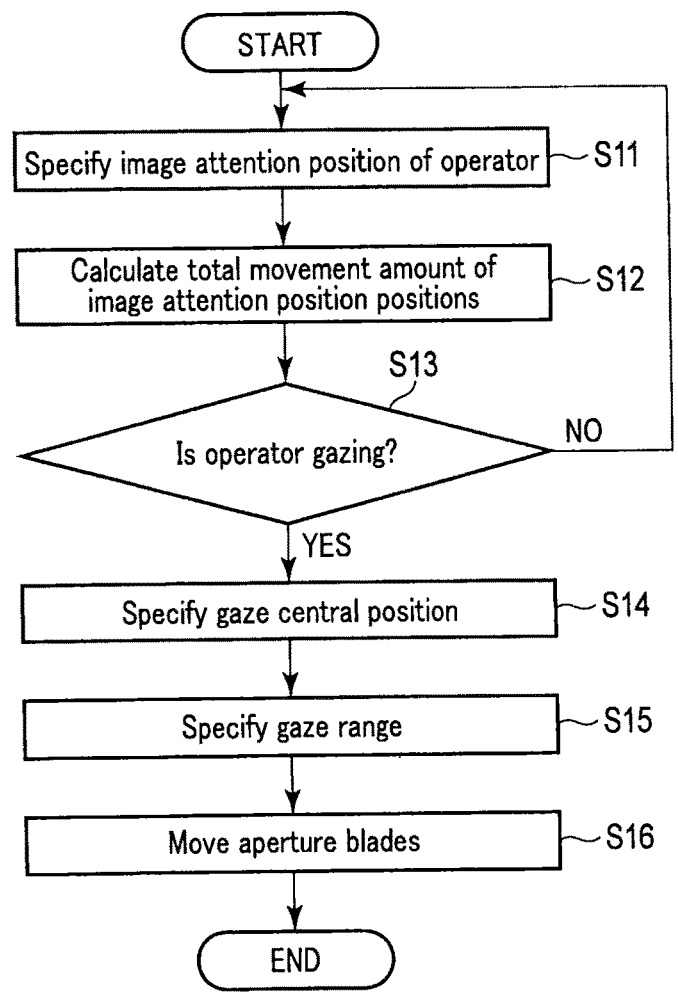
FIG. 9 is a flowchart for explaining positive beam limitation processing provided for the X-ray diagnostic apparatus according to the second embodiment.

FIG. 9 is a flowchart for explaining positive beam limitation processing provided for the X-ray diagnostic apparatus 2 according to the second embodiment.

(Step S11)

The stop control unit 14 converts a monitor attention position into an image attention position. This processing will specify the image attention position of the operator O.

(Step S12)

The calculation unit 25 calculates the total movement amount of a predetermined number of consecutive image attention positions. A predetermined number of consecutive image attention positions will be described with reference to FIG. 10.

Figure 10:
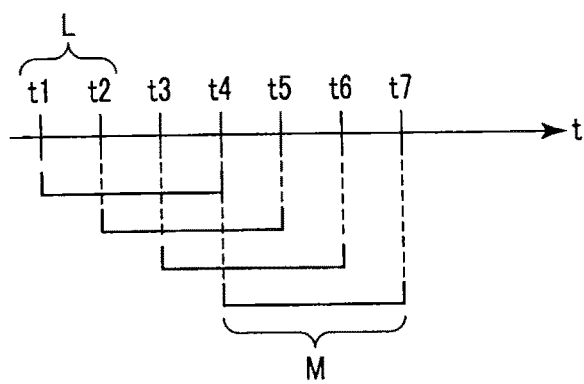
FIG. 10 is a view for explaining a predetermined number of image attention positions for the calculation of total movement amounts by a calculation unit.

FIG. 10 is a view for explaining a predetermined number of image attention positions for the calculation of a total movement amount by the calculation unit 25. FIG. 10 shows the timings at which the external attention position specifying unit 16 inputs monitor attention positions to the attention position input unit 24. For example, referring to FIG. 10, the attention position input unit 24 receives the data of a monitor attention position from time t1 in a cycle L. At this time, the attention position specifying unit 16 may specify a monitor attention position in the cycle L or specify a monitor attention position in a cycle shorter than the cycle L. Referring to FIG. 10, a predetermined number M is four. Therefore, the calculation unit 25 calculates a total movement amount for each predetermined number M, like calculating the total movement amount of an image attention position from time t1 to time t4 and the total movement amount of an image attention position from time t2 to time t5. Note that it is possible to change the predetermined number M, as needed, in accordance with an instruction from the operator O via the operation unit 23. In addition, the operator O may designate the predetermined number M with a time.

(Step S13)

The comparison unit 26 determines whether the operator O is gazing. If the comparison unit 26 determines that the operator O is gazing, the process shifts to step S14. If the comparison unit 26 determines that the operator O is not gazing, the process returns to step S11. Processing by the calculation unit 25 and the comparison unit 26 will be described with reference to FIG. 11.

FIGS. 11A, 11B, 11C, and 11D are respectively the first, second, third, and fourth views for explaining processing by the calculation unit 25 and the comparison unit 26 of the X-ray diagnostic apparatus 2 according to the second embodiment. FIGS. 11A, 11B, 11C, and 11D show the transition of the movement of an image attention position from time t1 to time t4. The calculation unit 25 specifies a movement amount between two image attention positions.

Figure 11A:
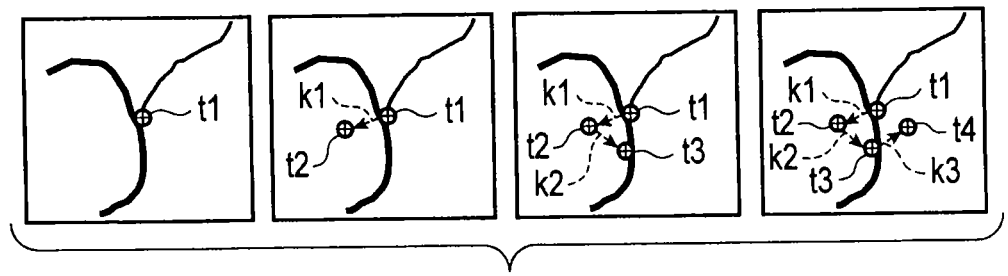
FIG. 11A is the first view for explaining processing by the calculation unit and comparison unit of the X-ray diagnostic apparatus according to the second embodiment.
Figure 11B:
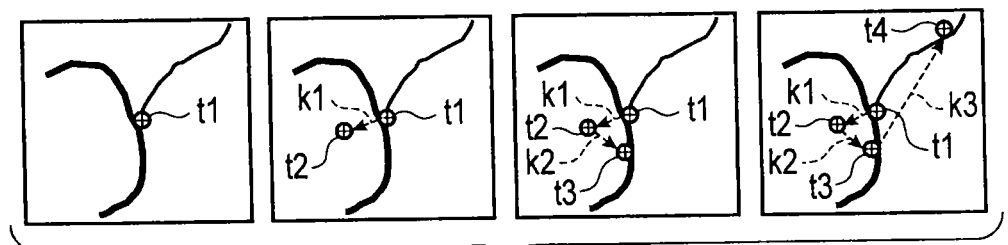
FIG. 11B is the second view for explaining processing by the calculation unit and comparison unit of the X-ray diagnostic apparatus according to the second embodiment.

For example, as shown in FIGS. 11A and 11B, the calculation unit 25 specifies a movement amount between two image attention positions respectively corresponding to two times adjacent to each other in a time series. More specifically, the calculation unit 25 calculates a movement amount k1 based on the coordinates of an image attention position corresponding to time t1 and the coordinates of an image attention position corresponding to time t2. The calculation unit 25 then calculates a total movement amount ks (the sum of k1, k2, and k3) by repeatedly executing the above processing from time t1 to time t4. The comparison unit 26 compares the total movement amount ks with a threshold kt. If the comparison result indicates that the total movement amount ks is less than the threshold kt as shown in FIG. 11A, the comparison unit 26 determines at time t4 that the operator O is gazing. When the total movement amount ks is less than the threshold kt, it indicates that the image attention position has not greatly moved. That is, it indicates that the operator O is gazing. In contrast to this, as shown in FIG. 11B, if the total movement amount ks is equal to or more than the threshold kt, the comparison unit 26 determines at time t4 that the operator O is not gazing. When the total movement amount ks is equal to or more than the threshold kt, it indicates that the image attention position has greatly moved. That is, it indicates that the operator O is not gazing.

Figure 11C:
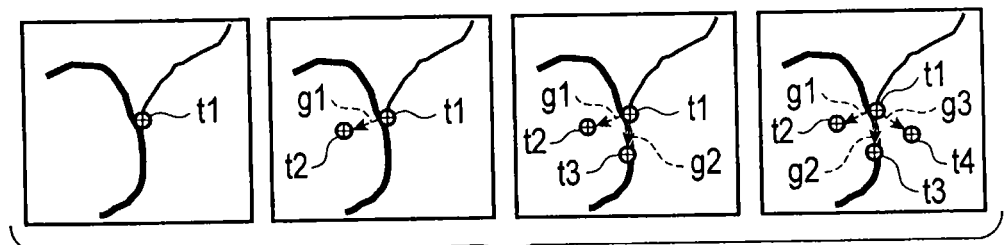
FIG. 11C is the third view for explaining processing by the calculation unit and comparison unit of the X-ray diagnostic apparatus according to the second embodiment.
Figure 11D:
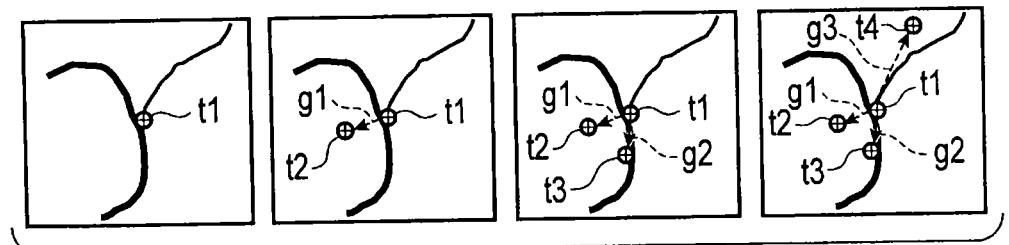
FIG. 11D is the fourth view for explaining processing by the calculation unit and comparison unit of the X-ray diagnostic apparatus according to the second embodiment.

Alternatively, for example, as shown in FIGS. 11C and 11D, the calculation unit 25 may calculate a movement amount between an image attention position corresponding to the start time point of the predetermined number M and another image attention position. More specifically, if time t1 is the start time point, the calculation unit 25 calculates a distance g1 of an image attention position corresponding to time t2 with respect to an image attention position corresponding to time t1. Likewise, the calculation unit 25 calculates a distance g2 of an image attention position corresponding to time t3 with respect to the image attention position corresponding to time t1. Likewise, the calculation unit 25 calculates a distance g3 of an image attention position corresponding to time t4 with respect to the image attention position corresponding to time t1. The comparison unit 26 compares a total movement amount s (the sum of g1, g2, and g3) with the threshold kt. If the comparison result indicates that the total movement amount gs is less than the threshold kt as shown in FIG. 11C, i.e., the image attention position has not greatly moved, the comparison unit 26 determines at time t4 that the operator O is gazing. In contrast to this, as shown in FIG. 11D, if the total movement amount gs is equal to or more than the threshold kt, i.e., the image attention position has greatly moved, the comparison unit 26 determines at time t4 that the operator O is not gazing.

(Step S14)

The stop control unit 14 specifies a gaze central position in the image coordinate system based on a predetermined number of image attention positions. A gaze central position will be described with reference to FIGS. 12A, 12B, and 12C.

Figure 12A:
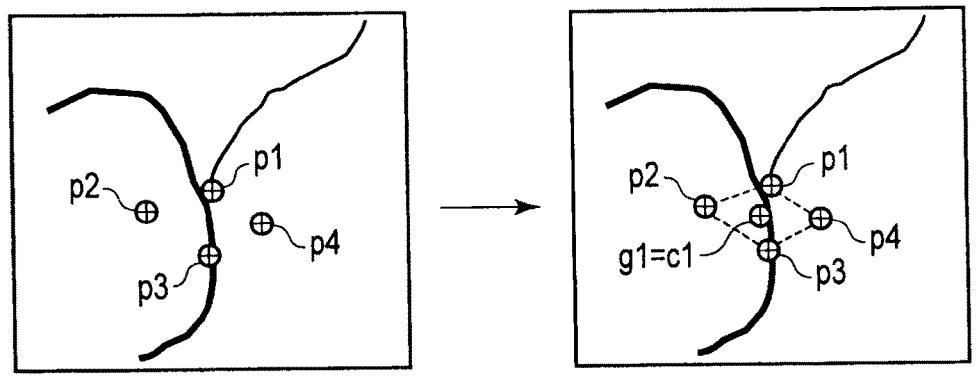
FIG. 12A is a view showing the first example of a gaze central position set by a stop control unit.
Figure 12B:
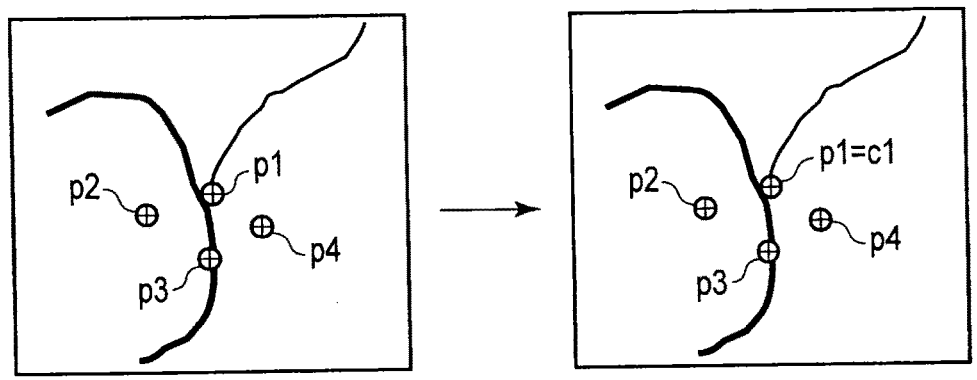
FIG. 12B is a view showing the second example of a gaze central position set by the stop control unit.
Figure 12C:
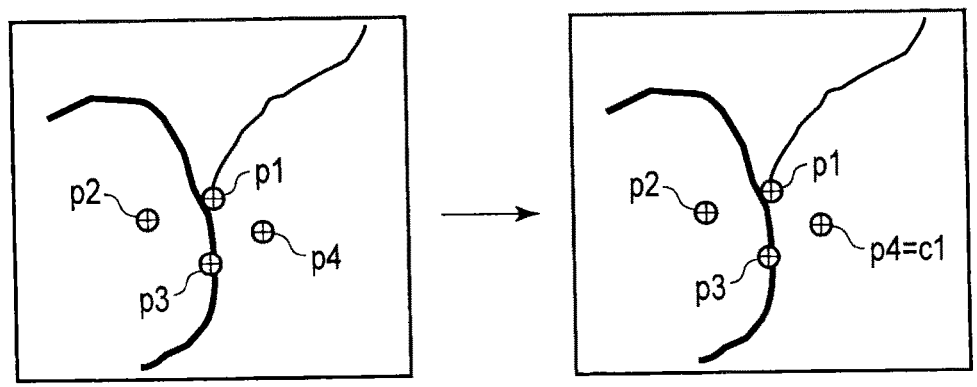
FIG. 12C is a view showing the third example of a gaze central position set by the stop control unit.

FIGS. 12A, 12B, and 12C respectively show the first, second, and third examples of gaze central positions set by the stop control unit 14. A predetermined number of image attention positions is four, which are respectively represented by p1, p2, p3, and p4. The order of p1, p2, p3, and p4 is in a time series.

As shown in FIG. 12A, the stop control unit 14 sets a barycentric position g1 determined by a predetermined number of image attention positions as a gaze central position c1. In addition, as shown in FIG. 12B, the stop control unit 14 sets, as the gaze central position c1, the image attention position p1, of the predetermined number of image attention positions, which is specified first. As shown in FIG. 12C, the stop control unit 14 sets, as the gaze central position c1, the latest image attention position p4 of the predetermined number of image attention positions. Note that if one attention position of the predetermined number of image attention positions is to be set as a gaze central position, the stop control unit 14 may set another image attention position, other than p1 and p4 described with reference to FIGS. 12B and 12C, as a gaze central position. It is possible to change an image attention position, as needed, to set, as a gaze central position, a specific one of a predetermined number of image attention positions in accordance with an instruction from the operator O via the operation unit 23.

(step S15)

The stop control unit 14 sets a gaze range in the image coordinate system. Methods of setting a gaze range include a method (1) using a gaze central position and a method (2) using a predetermined number of image attention positions. The method (1) will be described below with reference to FIGS. 13A and 13B.

FIG. 13A is a view showing the first example of a gaze range set by the stop control unit 14. As shown in FIG. 13A, the stop control unit 14 sets a gaze range a1 centered on a gaze central position c1. A vertical width t1 and a horizontal width w1 of the gaze range a1 are preset sizes. The widths t1 and w1 may be the same or changed as needed in accordance with instructions from the operator O via the operation unit 23.

FIG. 13B is a view showing the second example of the gaze range set by the stop control unit 14. As shown in FIG. 13B, the stop control unit 14 sets a gaze range a2 centered on a gaze central position c2. A vertical width t2 of the gaze range a2 is decided based on the farthest image attention position from the gaze central position c2 in the vertical direction. Likewise, a horizontal width w2 of the gaze range is decided based on the farthest image attention position from the gaze central position c2 in the horizontal direction. As shown in FIG. 13B, p1 represents the farthest image attention position from the gaze central position c1 in the vertical direction, and d1 represents the distance from the position p1. On the other hand, p4 represents the farthest image attention position from the gaze central position c2 in the horizontal direction, and d2 represents the distance from the position p4. That is, t2 is given by 2×d1, and w2 is given by 2×d2. Note that t2 and w2 may be the same width. At this time, t2 and w2 are decided based on the farthest image attention position from the gaze central position c2. For example, in the case shown in FIG. 13B, t2 and w2 are decided based on the farthest image attention position p4 from the gaze central position c2. The widths t2 and w2 are given by 2×d2.

The method (2) will be described next with referenced to FIGS. 14A and 14B.

FIGS. 14A and 14B are views showing the third and fourth examples of the gaze range set by the stop control unit 14. As shown in FIG. 14A, the stop control unit 14 sets a minimum rectangular range a3 including the image attention positions p1, p2, p3, and p4 as a gaze range. Therefore, the vertical width t3 of the gaze range a3 is set based on p1 and p3. On the other hand, the horizontal width w3 of the gaze range a3 is set based on p2 and p4. Note that the rectangular range a3 may have a square shape instead of the minimum rectangular shape. In this case, one side of a gaze range having a square shape is set to, for example, one of the widths of the vertical and horizontal sides which is longer than the other. As shown in FIG. 14B, the stop control unit 14 may set, as a gaze range, a range a4 obtained by extending the gaze range a3 set in FIG. 14A by a predetermined margin L in the four directions. The predetermined margin L is registered in the X-ray diagnostic apparatus 2 in advance. Note that the predetermined margin L may differ in the vertical and horizontal directions on an image.

(Step S16)

The aperture blades are moved to make the aperture have a range corresponding to the gaze range set in step S15. A method of moving the aperture blades using the stop control unit 14 will be described with reference to FIGS. 15A and 15B.

Figure 15A:
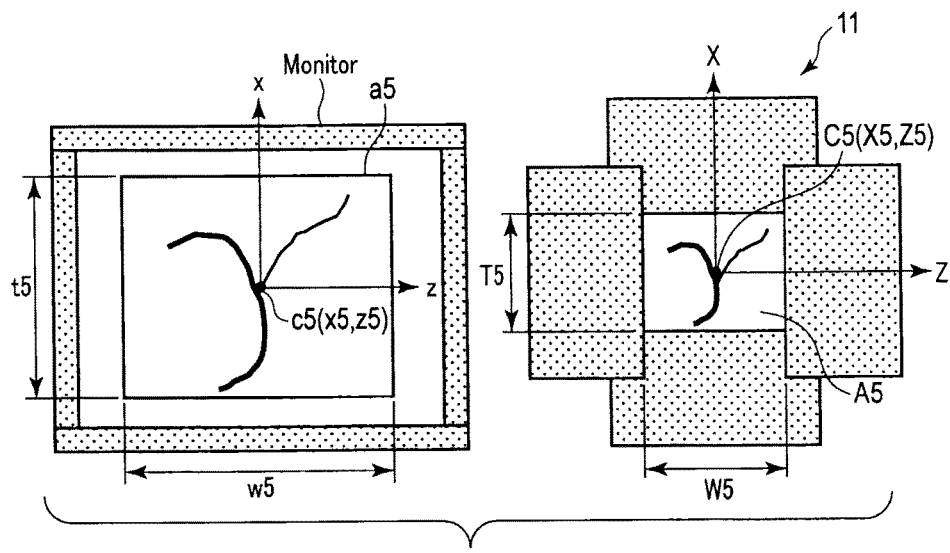
FIG. 15A is a view showing the X-ray image displayed on a monitor and the aperture of the stop unit before it is determined in step S13 that the operator is gazing.

FIG. 15A is a view showing the X-ray image displayed on the monitor 115 and the aperture of the stop unit 11 before it is determined in step S13 that the operator O is gazing. As shown in FIG. 15A, the image coordinate system is matched to the coordinate system of the stop unit 11 (to be referred to as the stop coordinate system hereinafter). That is, for example, a central position c5(x5, z5) of an X-ray image a5 corresponds to a central position C5(X5, Z5) of an aperture A5. At this time, the X-ray image a5 is a fluoroscopic image updated in real time. A vertical width t5 and a horizontal width w5 of the X-ray image a5 respectively correspond to a vertical width T5 and a horizontal width W5 of the aperture A5.

Figure 15B:
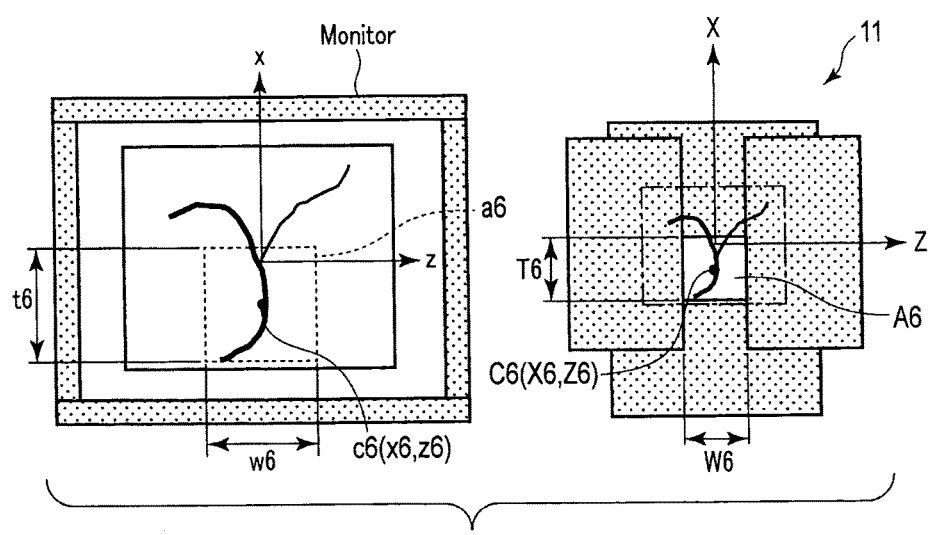
FIG. 15B is a view showing the X-ray image displayed on the monitor and the aperture of the stop unit after it is determined in step S13 that the operator is gazing.

FIG. 15B is a view showing the X-ray image displayed on the monitor 115 and the aperture of the stop unit 11 after it is determined in step S13 that the operator O is gazing. The stop control unit 14 has set a gaze central position c6(x6, z6) and a vertical width t6 and a horizontal width w6 of a gaze range a6. As shown in FIG. 15A, since the image coordinate system has already been matched to the stop coordinate system, the stop control unit 14 can convert the gaze central position c6(x6, z6) of the gaze range a6 into a central position C6(X6, Z6) of an aperture A6. Likewise, the stop control unit 14 can convert the vertical width t6 and the horizontal width w6 of the gaze range a6 into a vertical width T6 and a horizontal width W6 of the aperture A6. That is, for example, the gaze range a6 of the X-ray image corresponds to the aperture A6. The monitor 115 superimposes and displays a fluoroscopic image on an LIH image. The LIH image displayed in a range other than the gaze range a6 of the X-ray image. The fluoroscopic image updated in real time is displayed in a range corresponding to the gaze range a6. The stop control unit 14 moves the aperture blades of the stop unit 11 based on the central position C6, the vertical width T6, and the horizontal width W6 of the aperture A6.

With the processing from step S11 to step S16, the positive beam limitation processing is complete. Note that after the aperture is subjected to positive beam limitation, the monitor 115 superimposes and displays the fluoroscopic image of the range corresponding to the aperture of the stop unit 11 on the LIH image. The LIH image is an X-ray image concerning the object P immediately before the aperture is subjected to positive beam limitation.

(Automatic Tracking Function)

The automatic tracking function is a function of automatically moving the position of the aperture of the stop unit 11 in accordance with the image attention position of the operator O on the X-ray image displayed on the monitor 115 after the aperture of the stop unit 11 is subjected to positive beam limitation by the positive beam limitation function described above. Processing concerning the automatic tracking function (automatic tracking processing) will be described with reference to FIGS. 16A and 16B.

Figure 16A:
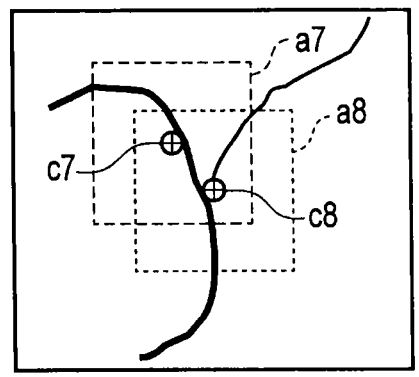
FIG. 16A is the first view for explaining automatic tracking processing.

FIG. 16A is the first view for explaining automatic tracking processing. Referring to FIG. 16A, c7 represents the gaze central position of the operator O at time t7, and a7 represents a gaze range corresponding to c7. Likewise, c8 represents the gaze central position of the operator O at time t8 later than time t7, and a8 represents a gaze range corresponding to c8. That is, FIG. 16A shows a state in which the gaze central position of the operator O has changed from c7 to c8.

The stop control unit 14 controls the stop unit 11 in response to the movement of the gaze central position from c7 to c8 so as to automatically move the central position of the aperture of the stop unit 11 from a position corresponding to the gaze central position c7 to a position corresponding to the gaze central position c8. In addition, the stop control unit 14 controls the stop unit 11 so as to change the size of the aperture from a size corresponding to the gaze range a7 to a size corresponding to the gaze range a8. At this time, the stop control unit 14 may control the stop unit 11 so as to move only the central position of the aperture while holding the size of the aperture corresponding to the gaze range a7. The above processing makes it possible to automatically move the position of the aperture of the stop unit 11 in accordance with the image attention position of the operator O on the X-ray image displayed on the monitor 115.

Note that in automatic tracking processing, the stop control unit 14 may decide, in accordance with the movement amount of an image attention position, whether to execute automatic tracking processing.

Figure 16B:
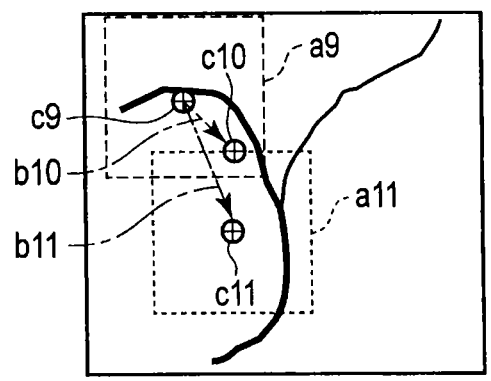
FIG. 16B is the second view for explaining automatic tracking processing.

FIG. 16B is the second view for explaining automatic tracking processing. Referring to FIG. 16B, c9 represents the gaze central position of the operator O at time t9, a9 represents a gaze range corresponding to c9, c10 represents the gaze central position of the operator O at time t10 later than time t9, c11 represents the gaze central position of the operator O at time t11 later than time t10, and a11 represents a gaze range corresponding to c11. That is, FIG. 16B shows a state in which the gaze central position of the operator O has changed from c9 to c10, and from c10 to c11.

The calculation unit 25 calculates the movement amount of a gaze central position. The comparison unit 26 compares the movement amount of the gaze central position with a threshold. The stop control unit 14 controls the stop unit 11 in accordance with the comparison result obtained by the comparison unit 26. More specifically, as shown in FIG. 16B, when the gaze central position has changed from c9 to c10, the calculation unit 25 calculates a movement amount b10 between c9 and c10. The comparison unit 26 compares the movement amount b10 with the threshold. If the movement amount b10 is less than the threshold, the stop control unit 14 holds the size and position of the aperture. That is, if the movement amount b10 is less than the threshold, the stop control unit 14 does not execute automatic tracking processing. At this time, the threshold is defined by, for example, the distance from the gaze central position to an end of the gaze range. With this operation, even when the gaze central position of the operator O moves, since the movement destination falls within the gaze range, the operator O can continuously see the fluoroscopic moving image without executing automatic tracking processing. This can decrease the number of times of control of the stop unit 11 by the stop control unit 14, and hence can reduce the load on the mechanism of the stop unit 11.

On the other hand, when the gaze central position has changed from c10 to c11, the calculation unit 25 calculates a movement amount b11 between c9 and c11. In this case, the calculation unit 25 calculates a movement amount between c9 and c11 instead of a movement amount between c10 and c11. This is because the position and size of the current aperture respectively correspond to the gaze central position c9 and the gaze range a9. For this reason, the calculation unit 25 calculates a movement amount from the gaze central position c9 to another gaze central position. The comparison unit 26 compares the movement amount b10 with the threshold. At this time, the threshold is defined by, for example, the distance from the gaze central position to an end of the gaze range. With this operation, when the gaze central position of the operator O moves and the movement designation falls outside the gaze range, it is possible to know that automatic tracking processing needs to be executed. If the movement amount b10 is equal to or more than the threshold, the stop control unit 14 executes automatic tracking processing. More specifically, the stop control unit 14 controls the stop unit 11 in response to the movement of the gaze central position from c10 to c11 so as to automatically move the central position of the aperture of the stop unit 11 from a position corresponding to the gaze central position c9 to a position corresponding to the gaze central position c11. In addition, the stop control unit 14 controls the stop unit 11 so as to change the size of the aperture from a size corresponding to the gaze range a9 to a size corresponding to the gaze range a11. At this time, the stop control unit 14 may control the stop unit 11 so as to move only the central position of the aperture while holding the size of the aperture corresponding to the gaze range a9.

(Automatic Enlargement Function)

The automatic enlargement function is a function of automatically enlarging the aperture of the stop unit 11 in accordance with the image attention position of the operator O on the X-ray image displayed on the monitor 115 after the aperture of the stop unit 11 is subjected to positive beam limitation by the positive beam limitation function described above. Processing concerning the automatic enlargement function (automatic enlargement processing) will be described with reference to FIGS. 17A, 17B, and 17C.

Figure 17A:
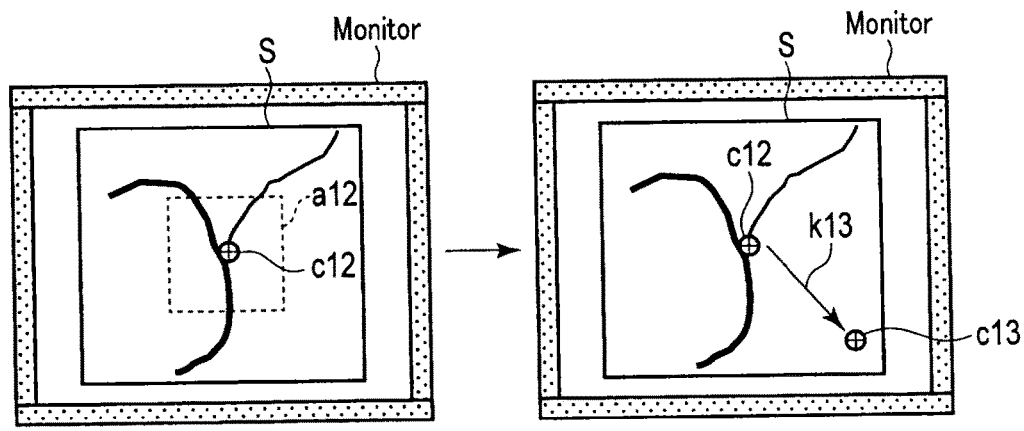
FIG. 17A is the first view for explaining automatic enlargement processing.

FIG. 17A is the first view for explaining automatic enlargement processing. Referring to FIG. 17A, c12 represents the gaze central position of the operator O at time t12, a12 represents a gaze range corresponding to c12, and c13 represents the gaze central position of the operator O at time t13 later than time t12. That is, FIG. 17A shows a state in which the gaze central position of the operator O has changed from c12 to c13. The calculation unit 25 calculates a movement amount k13 between the gaze central positions c12 and c13. The comparison unit 26 compares the movement amount k13 with the threshold. If the movement amount k13 is equal to or more than the threshold, the stop control unit 14 controls the stop unit 11 so as to enlarge the aperture of the stop unit 11. For example, as shown in FIG. 17A, the stop control unit 14 enlarges the aperture and moves the central position of the aperture so as to make the irradiation range correspond to an entire range S of an X-ray image in response to the movement of the gaze central position from c12 to c13.

Figure 17B:
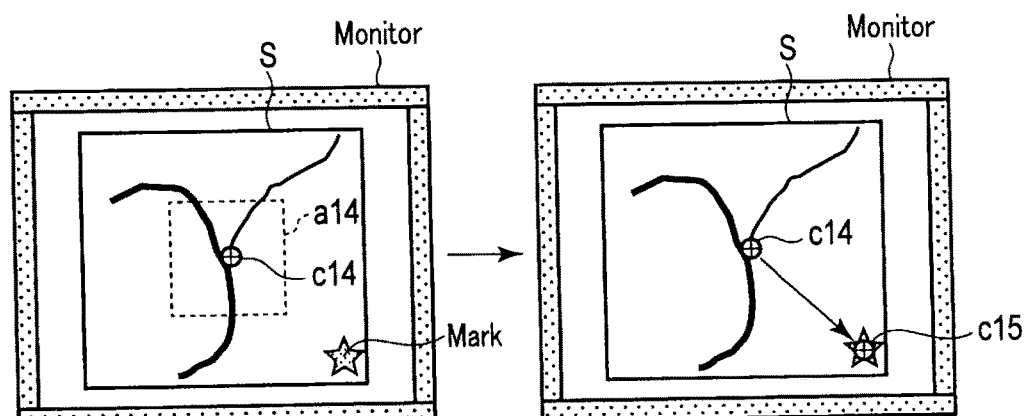
FIG. 17B is the second view for explaining automatic enlargement processing.

FIG. 17B is the second view for explaining automatic enlargement processing. Referring to FIG. 17B, the monitor 115 displays a mark on an X-ray image, c14 represents the gaze central position of the operator O at time t14, a14 represents a gaze range corresponding to c14, and c15 represents the gaze central position of the operator O at time t15 later than time t14. FIG. 17B shows a state in which the gaze central position of the operator O has changed from c14 to c15. The stop control unit 14 controls the stop unit 11 so as to enlarge the aperture of the stop unit 11, in response to when the operator O gazes at the mark displayed on the monitor 115, i.e., when the gaze central position is specified on the mark displayed on the monitor 115. As shown in FIG. 17B, for example, the stop control unit 14 enlarges the aperture and moves the central position of the aperture so as to make the irradiation range correspond to the entire range S of the X-ray image.

Figure 17C:
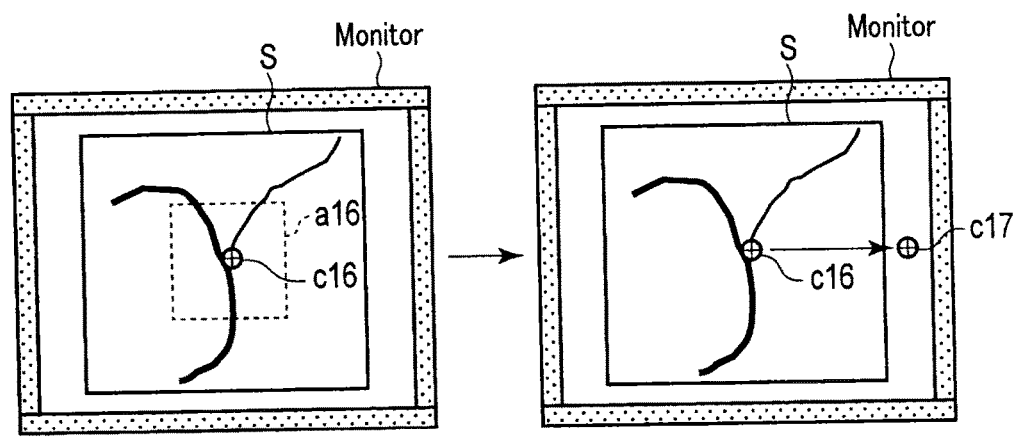
FIG. 17C is the third view for explaining automatic enlargement processing.

FIG. 17C is the third view for explaining automatic enlargement processing. Referring to FIG. 17C, c16 represents the gaze central position of the operator O at time t16, a16 represents a gaze range corresponding to c16, and c17 represents the gaze central position of the operator O at time t17 later than time t16. The gaze central position c17 falls outside the X-ray image. FIG. 17C shows a state in which the gaze central position of the operator O has changed from c16 to c17. As shown in FIG. 17C, when the gaze central position falls outside the X-ray image displayed on the monitor 115, the stop control unit 14 controls the stop unit 11 so as to enlarge the aperture of the stop unit 11. As shown in FIG. 17C, the stop control unit 14 enlarges the aperture and moves the central position of the aperture so as to make the irradiation range correspond to the entire range S of the X-ray image, in response to the movement of the gaze central position from c16 to c17.

The automatic enlargement function allows the operator O to temporarily see the overall state of the irradiation range by only shifting the gaze central position from the X-ray image, gazing at the mark on the monitor 115, or greatly moving the gaze central position.

Note that the movement of the gaze position of the operator O, which triggers automatic enlargement processing, may trigger another processing.

For example, the X-ray source control unit 13 may control the X-ray source 10 so as to decrease at least one of a tube voltage value and tube current voltage to be supplied to the X-ray source 10 and the pulse rate generated by the X-ray source 10. In addition, the stop control unit 14 may control the stop unit 11 so as to close the aperture of the stop unit 11. Therefore, the operator O can reduce unnecessary exposure on the object P by only shifting the gaze central position from the X-ray image, gazing at the mark on the monitor 115, or greatly moving the gaze central position.

The effects of the second embodiment will be described below.

The positive beam limitation function according to the second embodiment changes the position and size of the aperture of the stop unit 11 in accordance with the image attention position of the operator O on an X-ray image. More specifically, the position and size of the aperture of the stop unit 11 are changed in correspondence with a portion of the X-ray image to which the operator O is paying attention. At this time, X-rays are applied to only a range corresponding to the aperture. If the monitor 115 displays only the X-ray image of the range corresponding to the aperture of the stop unit 11, it is not possible to check a portion other than the image attention position. For this reason, the display control unit 27 displays, on the monitor 115, a fluoroscopic image corresponding to the aperture of the stop unit 11 on an LIH image immediately before positive beam limitation processing. This allows the operator O to check, on the LIH image, a portion other than a portion to which attention is paid while seeing a fluoroscopic image corresponding to the portion to which attention is paid. In addition, the automatic tracking function makes it possible to automatically move the position of the aperture of the stop unit 11 while moving a portion to which the operator O is paying attention, after positive beam limitation processing. That is, the operator O can reduce the exposure while concentrating on a procedure without being actively conscious of a reduction in exposure during the procedure.

When the operator is not seeing an X-ray image, it is possible to reduce unnecessary exposure on an object by changing X-ray conditions for the X-ray source 10 for the generation of an X-ray fluoroscopic moving image. This can also contribute to a reduction in power consumption.

(Third Embodiment)

An X-ray diagnostic apparatus according to the third embodiment will be described below, centered on differences from the second embodiment.

FIG. 18 is a schematic view showing an example of an X-ray diagnostic apparatus 3 according to the third embodiment. The X-ray diagnostic apparatus 2 according to the second embodiment is configured to change at least one of the size and position of the aperture of the stop unit 11 in accordance with a plurality of image attention positions, and hence the stop unit 11 is controlled by the stop control unit 14. In contrast to this, the X-ray diagnostic apparatus 3 according to the third embodiment is configured to move the position of the aperture of an X-ray filter 17 in accordance with a plurality of image attention positions, and hence the X-ray filter 17 is controlled by an X-ray filter control unit (X-ray filter control circuitry) 18.

In order to, for example, reduce the X-ray exposure dose of an object and improve image quality, the X-ray filter 17 of the X-ray diagnostic apparatus 3 according to the third embodiment changes the radiation quality of X-rays and removes long-wavelength components unnecessary for diagnosis from the continuous spectrum of X-rays exiting from the radiation window. The X-ray filter 17 partially reduces the dose of X-rays applied to the X-ray detection surface of an X-ray detection unit 12 (to be simply referred as the X-ray detection surface hereinafter). The X-ray filter 17 is moved under the control of the X-ray filter control unit 18.

FIGS. 19A, 19B, and 19C are views showing the first, second, and third examples of the X-ray filter 17 of the X-ray diagnostic apparatus 3 according to the third embodiment.

The X-ray filter 17 according to the first example shown in FIG. 19A is formed from a metal plate having an attenuation coefficient A, and has an aperture. For example, the aperture is formed such that the central position of the aperture overlaps the central position of the overall X-ray filter 17. The aperture has, for example, a rectangular shape, as shown in FIG. 19A. However, the aperture may have another shape such as a circular shape. The irradiation range of X-rays passing through the X-ray filter 17 according to the first example shown in FIG. 19A is constituted by an irradiation range corresponding to the aperture of the X-ray filter 17 and another irradiation range. The irradiation range corresponding to the aperture is generated by X-rays which do not pass through the X-ray filter 17. The other irradiation range is generated by the X-rays passing through the X-ray filter 17. For this reason, the dose of X-rays in the other irradiation range is reduced as compared with the dose of X-rays in the irradiation range corresponding to the aperture. Note that the X-ray filter 17 according to the first example may itself be one component having an aperture. In addition, the X-ray filter 17 according to the first example may form an aperture by being constituted by a plurality of components. In this case, an operator O can change the size, shape, and the like of an aperture by interchanging at least one of the plurality of components.

The X-ray filter 17 according to the second example shown in FIG. 19B has an arrangement obtained by combining the X-ray filter 17 according to the first example with another X-ray filter 17. The other X-ray filter 17 is formed from a metal plate having an attenuation coefficient B. The irradiation range of X-rays passing through the X-ray filter 17 according to the second example shown in FIG. 19B is constituted by an irradiation range corresponding to the aperture of the X-ray filter 17 and another irradiation range. The irradiation range corresponding to the aperture is generated by X-rays passing through the other X-ray filter 17. On the other hand, the other irradiation range is generated by X-rays passing through the X-ray filter 17 according to the first example and the other X-ray filter 17. For this reason, the dose of X-rays in the irradiation range corresponding to the aperture is reduced compared with the dose of X-rays without the X-ray filter 17. In addition, the dose of X-rays in the other irradiation range is reduced as compared with the dose of X-rays in the irradiation range corresponding to the aperture. Although the other X-ray filter 17 is one filter in FIG. 19B, the other X-ray filter 17 may include a plurality of filters.

The X-ray filter 17 according to the third example shown in FIG. 19C is formed from a metal plate and has a plurality of portions with different attenuation coefficients in the same plane. For example, as shown in FIG. 19C, the X-ray filter 17 according to the third example has, in the same plane, the first portion having an attenuation coefficient A and the second portion which is in contact with the circumference of the first portion and has an attenuation coefficient B. The irradiation range corresponding to the first portion is generated by X-rays passing through the portion with the attenuation coefficient A. On the other hand, the irradiation range corresponding to the second portion is generated by X-rays passing through the portion with the attenuation coefficient B. For this reason, the X-ray filter 17 according to the third example forms two irradiation ranges having different doses with respect to the overall irradiation range. The doses of the two irradiation ranges are decided in accordance with the attenuation coefficients A and B. If, for example, the attenuation coefficient B is larger than the attenuation coefficient A, in the X-ray filter 17 according to the third example, the dose of X-rays in the irradiation range corresponding to the second portion is reduced as compared with the dose of X-rays in the irradiation range corresponding to the first portion surrounded by the second portion with respect to the overall irradiation range. Note that the X-ray filter 17 according to the third example may have a plurality of portions having different attenuation coefficients, and the plurality of portions may be, for example, two or three portions. In addition, the X-ray filter 17 according to the third example may have another arrangement as long as it can partially reduce the dose of X-rays with respect to the overall irradiation range. For example, the X-ray filter 17 according to the third example may be a metal plate which partially varies in thickness. Referring to FIG. 19C, the metal of the second portion may have a thickness larger than that of the metal of the first portion. Alternatively, the thickness of the X-ray filter 17 may increase stepwise from its central position to the edge of the X-ray filter 17.

Furthermore, the X-ray filter 17 may have a structure capable of changing the size and position of its aperture.

Figure 20A:
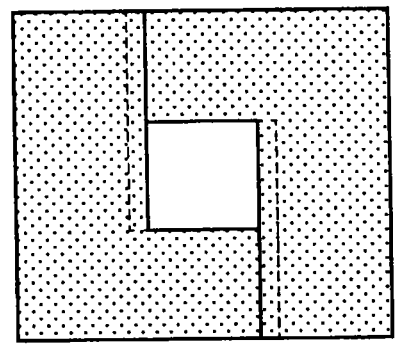
FIG. 20A is a view showing the first example of an X-ray filter having a structure capable of changing the size and position of an aperture.
Figure 20B:
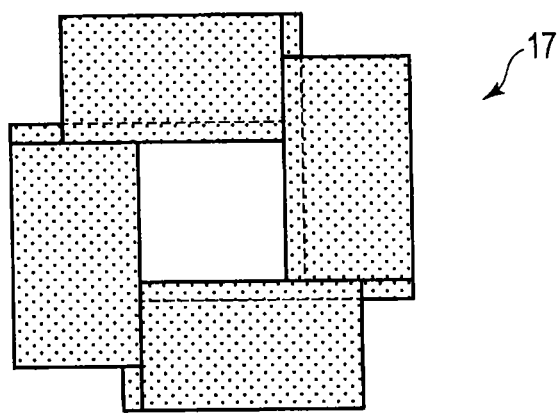
FIG. 20B is a view showing the second example of the X-ray filter having the structure capable of changing the size and position of the aperture.

FIGS. 20A and 20B are views showing the first and second examples of the X-ray filter 17 having a structure capable of changing the size and position of its aperture.

As shown in FIG. 20A, the X-ray filter 17 is constituted by the first and second components. The first and second components are formed from L-shaped metal plates having the same attenuation coefficient. As shown in FIG. 20A, the first and second components engage with each other to form the aperture of the X-ray filter 17. The X-ray filter control unit 18 moves the first and second components to enable the X-ray filter 17 shown in FIG. 20A to change the size and position of aperture in the X direction.

As shown in FIG. 20B, the X-ray filter 17 has four components formed from metal plates having the same attenuation coefficient, which engage with each other to form an aperture. The X-ray filter control unit 18 moves the four components to enable the X-ray filter 17 shown in FIG. 20B to change the size and position of aperture in at least one of the X direction and the Z direction.

The X-ray filter control unit 18 converts a monitor attention position expressed by the coordinate system of a monitor 115 into an image attention position expressed by the image coordinate system. An external attention position specifying unit 16 repeatedly inputs monitor attention position data to an attention position input unit 24 in a specific cycle. The X-ray filter control unit 18 converts a plurality of monitor attention positions constituting a time series into a plurality of corresponding image attention positions, respectively. In addition, the X-ray filter control unit 18 decides the central position of the aperture of the X-ray filter 17 based on a plurality of image attention positions constituting a time series. The X-ray filter control unit 18 then controls the X-ray filter 17 in accordance with the decided central position of the aperture.

FIG. 21 is a view for explaining the irradiation range of X-rays in the use of the X-ray filter 17 of the X-ray diagnostic apparatus 3 according to the third embodiment. Note that the irradiation range in FIG. 21 will be described by taking the X-ray filter 17 in FIG. 19B as an example.

FIG. 21 shows the irradiation range of the X-rays generated from the X-ray source 10 and transmitted through the X-ray filter 17. The X-ray filter 17 is constituted by a first X-ray filter 17A having no aperture and a second X-ray filter 17B having an aperture. As shown in FIG. 21, an irradiation range E of X-rays has two irradiation ranges with different doses. An irradiation range EH corresponding to the aperture of the second X-ray filter 17B is larger in the dose of X-rays than another irradiation range EL. The X-ray filter control unit 18 can move the irradiation range EH corresponding to the aperture of the second X-ray filter 17B by moving the second X-ray filter 17B in the X and Z directions. In addition, the X-ray filter control unit 18 can change the size of the irradiation range EH corresponding to the aperture of the second X-ray filter 17B by moving the second X-ray filter 17B in the Y direction. In addition, the X-ray filter control unit 18 may change the size and position of the aperture of the second X-ray filter 17B by moving the components constituting the X-ray filter 17 which are shown in FIGS. 20A and 20B.

An operation unit 23 accepts, from the operator O, an instruction to switch ON/OFF the X-ray filter 17 having the aperture (to be referred to as the aperture filter hereinafter).

The display control unit 27 displays a fluoroscopic image on the monitor 115. The images displayed on the monitor 115 will be described with reference to FIGS. 22A and 22B.

FIG. 22A is a view showing an example of the X-ray image displayed on the monitor 115 when the aperture filter of the X-ray diagnostic apparatus 3 according to the third embodiment is switched OFF. As shown in FIG. 22A, the monitor 115 displays an X-ray fluoroscopic image S1. Referring to FIG. 22A, since the aperture filter is switched OFF, the X-ray fluoroscopic image S1 generated by the X-ray generation unit has a uniform image level. The image level indicates image quality such as an S/N ratio or luminance.

FIG. 22B is a view showing an example of the X-ray image displayed on the monitor 115 when the aperture filter of the X-ray diagnostic apparatus 3 according to the third embodiment is switched ON. As shown in FIG. 22B, the monitor 115 displays an X-ray fluoroscopic image S2. Referring to FIG. 22B, since the aperture filter is switched ON, the X-ray fluoroscopic image S2 generated by the X-ray generation unit has two ranges with different image levels. As shown in FIG. 22B, the X-ray fluoroscopic image S2 has a range fa1 corresponding to the aperture of the aperture filter and a range fa2 corresponding to another portion of the aperture filter. A central position fc1 of the range fa1 corresponds to the central position of the aperture of the aperture filter. The size of the range fa1 corresponds to the size of the aperture of the aperture filter. The range fa1 of the X-ray fluoroscopic image corresponds to an irradiation range with a high dose, and the range fa2 of the X-ray fluoroscopic image corresponds to an irradiation range with a low dose. For this reason, the image level in the range fa1 of the X-ray fluoroscopic image is higher than that in the range fa2. As described in the first embodiment, an image processing unit (image processing circuitry) 22 may execute different types of image processing for X-ray fluoroscopic image data corresponding to the range fa1 and X-ray fluoroscopic image data corresponding to the range fa2 so as to match the image level in the range fa1 of the X-ray fluoroscopic image with that in the range fa2. The image processing unit 22 executes image processing based on the signal detected by the X-ray detection unit 12 in the irradiation range corresponding to the aperture of the X-ray filter 17 and the signal detected by the X-ray detection unit 12 in the irradiation range corresponding to another portion of the X-ray filter 17.

Note that when the aperture filter is switched OFF, the X-ray filter control unit 18 may automatically move the aperture filter so as to prevent X-rays from passing through the aperture filter. In addition, when the size of the aperture can be automatically changed, the X-ray filter control unit 18 may automatically increase the aperture so as to prevent X-rays from passing through the aperture filter. Furthermore, the aperture filter may be switched ON/OFF depending on whether the operator O inserts the aperture filter.

The X-ray diagnostic apparatus 2 according to the second embodiment reduces the exposure on the object P by automatically changing the position and size of the aperture of the stop unit 11 in accordance with the image attention position of the operator O. At this time, the monitor 115 superimposes and displays a fluoroscopic image corresponding to the aperture of the stop unit 11 on an LIH image. The operator O can fluoroscopically view only a portion to which he/she is paying attention.

As in the second embodiment, the X-ray diagnostic apparatus 3 according to the third embodiment can automatically change at least one of the position and size of the aperture of the X-ray filter 17 in accordance with the image attention position of the operator O. It is therefore possible to reduce the exposure on the object P, as in the second embodiment. A method of controlling the X-ray filter 17 by the X-ray filter control unit 18 is the same as the method of controlling the stop unit 11 by the stop control unit 14 of the X-ray diagnostic apparatus 2 according to the second embodiment. Note however that when using the X-ray filter 17 in FIGS. 19A, 19B, and 19C which can change only the position of the aperture of the X-ray filter 17, the X-ray filter control unit 18 performs only movement control of the position of the aperture of the X-ray filter 17.

The effects of the third embodiment will be described below.

The positive beam limitation function according to the third embodiment automatically changes the position and size of the aperture of the X-ray filter 17 in accordance with the image attention position on an X-ray image to which the operator O is paying attention. More specifically, the position and size of the aperture of the X-ray filter 17 are changed in accordance with a portion of an X-ray image to which the operator O is paying attention. At this time, the X-ray irradiation range includes a range with a high dose of X-rays passing through the aperture of the X-ray filter 17 and a range with a low dose of X-rays passing through a portion other than the aperture of the X-ray filter 17. The monitor 115 displays a fluoroscopic image. The fluoroscopic image has two ranges with different image levels. The image level in a range corresponding to a portion other than the aperture of the X-ray filter 17 is lower than that in a range corresponding to the aperture of the X-ray filter 17. However, the portion to which the operator O is paying attention corresponds to the aperture of the X-ray filter 17. For this reason, the monitor 115 displays a fluoroscopic image of the portion to which the operator O is paying attention and a fluoroscopic image of the portion to which no attention is paid. Even when the image of the portion to which no attention is paid has changed, the operator O can quickly handle it. In addition, the automatic tracking function makes it possible to automatically move the position of the aperture of the X-ray filter 17 while moving the portion to which the operator O is paying attention after positive beam limitation processing. That is, the operator O can reduce the exposure while concentrating on a procedure without being actively conscious of a reduction in exposure during the procedure.

(Fourth Embodiment)

The first embodiment, the second embodiment, and the third embodiment each have exemplified the single-plane X-ray diagnostic apparatus including one set of an X-ray imaging system including the X-ray source 10 and the X-ray detection unit 12. However, the first embodiment, the second embodiment, and the third embodiment are not limited to this. For example, the first embodiment, the second embodiment, and the third embodiment can be applied to even an X-ray diagnostic apparatus including a plurality of sets of X-ray imaging systems.

FIG. 23 is a schematic view showing an example of an X-ray diagnostic apparatus 4 according to the fourth embodiment. The X-ray diagnostic apparatus 4 according to the fourth embodiment shown in FIG. 23 is a biplane X-ray diagnostic apparatus including two imaging systems. This embodiment can also be applied to a stereo X-ray diagnostic apparatus as long as it includes a plurality of imaging systems. Each type of processing by a system control unit 20, a stop control unit 14, an X-ray filter control unit 18, and a display control unit 27 will be described below, centered on differences from the single-plane X-ray diagnostic apparatus. The fourth embodiment will exemplify a case in which the X-ray diagnostic apparatus 2 according to the second embodiment is applied to a biplane scheme.

The biplane X-ray diagnostic apparatus 4 according to the fourth embodiment (to be simply referred to as the biplane X-ray diagnostic apparatus 4 hereinafter) includes two imaging systems. Two Xs include, for example, a first imaging system 5 as a frontal system (frontal: F) and a second imaging system 6 as a lateral system (lateral: L). The two imaging systems are configured to make their isocenters coincide with each other. The two imaging systems are often configured such that two imaging directions respectively corresponding to the two imaging systems become perpendicular to each other.

FIG. 24 is a block diagram showing an example of the first imaging system 5 and the second imaging system 6.

The first imaging system 5 includes a first X-ray source 51, a first stop unit 52, and a first X-ray detection unit 53. The second imaging system 6 includes a second X-ray source 61, a second stop unit 62, and a second X-ray detection unit (second X-ray detection circuitry) 63. The first X-ray detection unit 53 detects the X-rays generated from the first X-ray source 51. The first stop unit 52 limits the size and central position of an irradiation range on the X-ray detection surface of the first X-ray detection unit 53. Likewise, the second X-ray detection unit 63 detects the X-rays generated from the second X-ray source 61. The second stop unit 62 limits the size and central position of an irradiation range on the X-ray detection surface of the second X-ray detection unit 63. An X-ray source control unit 13 controls the first X-ray source 51 and the second X-ray source 61. Control of the first X-ray source 51 and the second X-ray source 61 which is performed by the X-ray source control unit 13 includes, for example, control of a tube voltage value and a tube current value and control of a pulse rate. The stop control unit 14 controls the first stop unit 52 and the second stop unit 62. The stop control unit 14 decides the size and central position of the aperture of the first stop unit 52 based on a plurality of image attention positions constituting a time series. The stop control unit 14 also decides the size and central position of the aperture of the second stop unit 62 based on a plurality of image attention positions constituting a time series. The stop control unit 14 controls the first stop unit 52 and the second stop unit 62 in accordance with the respective decided sizes and central positions of the apertures.

An image generation unit (image generation circuitry) 21 generates the first X-ray image of the object P based on the data of X-rays detected by the first X-ray detection unit (first X-ray detection circuitry) 53. The image generation unit 21 generates the second X-ray image of the object P based on the data of X-rays detected by the second X-ray detection unit 63. The first X-ray image and the second X-ray image are obtained by imaging the object P from two imaging directions. The first X-ray image corresponds to the imaging direction of the first imaging system 5. The second X-ray image corresponds to the imaging direction of the second imaging system 6.

A display control unit 27 displays the first X-ray image and the second X-ray image on a monitor 115. The monitor 115 may include a monitor which displays the first X-ray image and a monitor which displays the second X-ray image. In addition, one monitor may be used as the monitor 115. In this case, for example, the first X-ray image and the second X-ray image are displayed side by side on the monitor 115.

Processing by the stop control unit 14 of the biplane X-ray diagnostic apparatus 4 according to the fourth embodiment will be described below with reference to the accompanying drawings.

FIG. 25A is the first view for explaining processing by the stop control unit 14 of the biplane X-ray diagnostic apparatus 4 according to the fourth embodiment.

Referring to FIG. 25A, the display control unit 27 displays a first X-ray image S1 and a second X-ray image S2 on the monitor 115. The gaze central position of an operator O is now at c20 on the second X-ray image. At this time, the stop control unit 14 decides a gaze range a20. The stop control unit 14 then controls the second stop unit 62 so as to make the central position of the aperture of the second stop unit 62 correspond to c20 and make the size of the aperture of the second stop unit 62 correspond to the gaze range a20. In addition, the stop control unit 14 controls the first stop unit 52 so as to close the aperture of the first stop unit 52. With the above processing by the stop control unit 14, the monitor 115 displays an LIH image corresponding to the first imaging system 5. In addition, a fluoroscopic image corresponding to the aperture of the second stop unit 62 is superimposed and displayed on the LIH image corresponding to the second imaging system 6. The operator O can check the fluoroscopic image of the gaze range of the X-ray image to which attention is currently paid. At this time, the object P is hardly exposed to X-rays from the first imaging system 5. In addition, since the second imaging system 6 irradiates only the gaze range with X-rays, the exposure on the object P can be reduced as compared with when the overall irradiation range is irradiated with X-rays.

Note that according to the above description, the stop control unit 14 closes the aperture of the first stop unit 52. However, as described below, the X-ray source control unit 13 may control the first X-ray source 51. For example, the X-ray source control unit 13 may control the first X-ray source 51 so as to decrease at least one of a tube voltage value and tube current value to be supplied to the first X-ray source 51 and the pulse rate generated by the first X-ray source 51. The X-ray source control unit 13 may also control the first X-ray source 51 to stop the operation of the first X-ray source 51.

FIG. 25B is the second view for explaining processing by the stop control unit 14 of the biplane X-ray diagnostic apparatus 4 according to the fourth embodiment.

Referring to FIG. 25A, the stop control unit 14 decides the gaze range a20 on the second X-ray image S2 in accordance with the gaze central position c20 on the second X-ray image S2. Referring to FIG. 25B, upon deciding the gaze range a20 on the second X-ray image S2 in accordance with the gaze central position c20 on the second X-ray image S2, the stop control unit 14 decides a gaze range a21 on the first X-ray image S1 based on the gaze range a20 on the second X-ray image S2.

FIG. 25C is the third view for explaining processing by the stop control unit 14 of the biplane X-ray diagnostic apparatus 4 according to the fourth embodiment.

Referring to FIG. 25C, as in FIG. 25B, the stop control unit 14 decides a gaze range a22 on the first X-ray image S1 based on the gaze range a20 on the second X-ray image S2. The gaze range a22 differs from the gaze range a21 in FIG. 25B in that the shape of the range is not rectangular. A method of deciding, based on a gaze range on one X-ray image, a gaze range on another X-ray image will be described with reference to FIG. 26.

FIG. 26 is a view for explaining a method of deciding, based on a gaze range on one X-ray image, a gaze range on another X-ray image. FIG. 26 shows how the object P is imaged by the first imaging system 5 and the second imaging system 6. The first imaging system 5 irradiates a range T1 with X-rays. The second imaging system 6 irradiates a range T2 with X-rays. The irradiation ranges T1 and T2 respectively correspond to the X-ray images S1 and S2 in FIG. 25.

First of all, upon deciding the gaze range a20, the stop control unit 14 specifies an irradiation range A20 corresponding to the gaze range a20. The stop control unit 14 then controls the second stop unit 62 to move the aperture blades of the second stop unit 62 so as to irradiate the irradiation range A20 with X-rays (step S40).

The stop control unit 14 then specifies a gaze region PF of the object P based on the imaging angle of the object P imaged by the first imaging system 5, the imaging angle of the object P imaged by the second imaging system 6, and the irradiation range of X-rays from the second imaging system 4. The gaze region PF is a range where the irradiation range of X-rays from the first imaging system 5 overlaps the irradiation range of X-rays from the second imaging system 6 after step S40.

The stop control unit 14 then controls the first stop unit 52 to move the aperture blades of the first stop unit 52 so as to form the irradiation range into a rectangular shape including at least the gaze region PF (step S41a). With this operation, a range A21 is set as the irradiation range of X-rays from the first imaging system 5. As shown in FIG. 25B, the range a21 on the first X-ray image S1 which corresponds to the irradiation range A21 becomes a gaze range, in which a fluoroscopic image is displayed.

Note that step S41a may be replaced with step S41b described below. In step S41b, the stop control unit 14 controls the first stop unit 52 to move the aperture blades of the first stop unit 52 so as to match the gaze region PF with an irradiation range. With this operation, a range A22 is set as the irradiation range of X-rays from the first imaging system 5. The irradiation range A22 has a trapezoidal shape. As shown in FIG. 25C, the range a22 on the first X-ray image S1 which corresponds to the irradiation range A22 becomes a gaze range, in which a fluoroscopic image is displayed.

Figure 27:
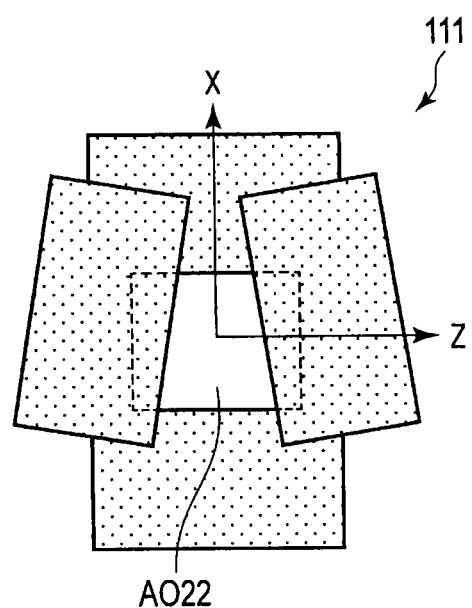
FIG. 27 is a view showing an example of the positions of the aperture blades of a first stop unit 52 in step S41b.

FIG. 27 is a view showing an example of the positions of the aperture blades of the first stop unit 52 in step S41b. As shown in FIG. 27, in step S41b, the stop control unit 14 moves each aperture blade of the first X-ray source 51 to match an aperture A022 with the irradiation range A22. As a result, one of the two pairs of aperture blades is arranged to be tilted with respect to the X-axis and the Z-axis.

With the above processing, as shown in FIGS. 25B and 25C, the gaze range a20 on the second X-ray image S2 and the gaze range a21 on the first X-ray image S1 are decided in accordance with the gaze central position c20 on the second X-ray image S2, and fluoroscopic images corresponding to the respective gaze ranges are displayed on the display unit 15.

As described above, the biplane X-ray diagnostic apparatus 4 according to the fourth embodiment can obtain the same effects as those of the X-ray diagnostic apparatus 2 according to the second embodiment. In addition, the biplane X-ray diagnostic apparatus 4 according to the fourth embodiment can decide gaze ranges on the two X-ray images displayed on the monitor 115 in accordance with the gaze central position on one of the X-ray images. This allows the operator O to fluoroscopically view, from different directions, a portion to which he/she is currently paying attention.

While certain embodiments have been described, these embodiments have been presented by way of example only, and are not intended to limit the scope of the inventions. Indeed, the novel embodiments described herein may be embodied in a variety of other forms; furthermore various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
an X-ray source configured to generate X-rays;
a plurality of lead plates including an aperture which narrows an irradiation range of X-rays with which an object is irradiated by the X-ray source; and
processing circuitry configured to:
specify, using a camera, an attention position based on a line of sight of an observer, and
perform movement control of the plurality of lead plates based on the specified attention position.

2. The X-ray diagnostic apparatus of claim 1, wherein the processing circuitry is configured to:
detect X-rays transmitted through the object, and
generate an X-ray image of the object based on a detection result of X-rays transmitted through the object,
wherein the processing circuitry controls the plurality of lead plates in accordance with an attention position of an observer on the X-ray image displayed on a monitor in order to move a position of the aperture or change a size of the aperture.

3. The X-ray diagnostic apparatus of claim 2, further comprising a display including attention position specifying circuitry,
wherein the attention position specifying circuitry specifies an attention position of the observer on an X-ray image displayed on the monitor by specifying a line of sight of the observer with respect to the display.

4. The X-ray diagnostic apparatus of claim 2, wherein the processing circuitry
repeatedly specifies an attention position of the observer, and
decides a position of the aperture and a size of the aperture in accordance with a predetermined number of consecutive attention positions of a plurality of attention positions constituting a time series.

5. The X-ray diagnostic apparatus of claim 2, wherein the processing circuitry is configured to:
calculate a total movement amount of the predetermined number of attention positions, and
compare the total movement amount with a threshold,
wherein the processing circuitry controls the plurality of lead plates in accordance with the predetermined number of attention positions to move the position of the aperture, when the total movement amount is less than the threshold.

6. The X-ray diagnostic apparatus of claim 5, wherein the processing circuitry controls the plurality of lead plates in accordance with the predetermined number of attention positions to narrow the aperture by moving the position of the aperture, when the total movement amount is less than the threshold.

7. The X-ray diagnostic apparatus of claim 4, wherein the processing circuitry is configured to:
calculate a total movement amount of the predetermined number of attention positions, and
compare the total movement amount with a threshold,
wherein the processing circuitry controls the plurality of lead plates in accordance with the predetermined number of attention positions to enlarge the aperture, when the total movement amount is not less than the threshold.

8. The X-ray diagnostic apparatus of claim 4, wherein the processing circuitry is configured to control the X-ray source to decrease at least one of a tube voltage value and tube current value to be supplied to the X-ray source and a pulse rate when each of the predetermined number of attention positions falls outside an X-ray image displayed on the monitor.

9. The X-ray diagnostic apparatus of claim 5, wherein the processing circuitry controls the plurality of lead plates such that an irradiation range corresponding to the aperture includes at least the predetermined number of attention positions.

10. The X-ray diagnostic apparatus of claim 5, wherein the processing circuitry controls the plurality of lead plates to match a central position of the aperture with one of the predetermined number of attention positions.

11. An X-ray diagnostic apparatus comprising:
an X-ray source configured to generate X-rays;
an X-ray filter arranged between the X-ray source and an object and including an aperture, the aperture including a movable structure; and
processing circuitry configured to:
detect X-rays transmitted through the object,
generate an X-ray image of the object based on a detection result of X-rays transmitted through the object,
specify, using a camera, an attention position based on a line of sight of an observer, and
control the X-ray filter in accordance with specified attention position of the observer on an X-ray image displayed on a monitor to move the position of the aperture.

12. The X-ray diagnostic apparatus of claim 11, wherein the processing circuitry
repeatedly specifies an attention position of the observer, and
decides a position of the aperture in accordance with a predetermined number of consecutive attention positions of a plurality of attention positions constituting a time series.

13. The X-ray diagnostic apparatus of claim 12, wherein the processing circuitry is configured to:
calculate a total movement amount of the predetermined number of attention positions, and
compare the total movement amount with a threshold,
wherein the processing circuitry controls the X-ray filter in accordance with the predetermined number of attention positions to move the position of the aperture, when the total movement amount is less than the threshold.

14. The X-ray diagnostic apparatus of claim 12, wherein the processing circuitry is configured to:
calculate a total movement amount of the predetermined number of attention positions, and
compare the total movement amount with a threshold,
wherein the processing circuitry switches OFF the X-ray filter, when the total movement amount is not less than the threshold.

15. The X-ray diagnostic apparatus of claim 11, wherein the processing circuitry is configured to execute different types of image processing for data of a range, of an X-ray image generated by the processing circuitry, which corresponds to the aperture and data of another range based on a signal detected by the processing circuitry in an irradiation range of the X-rays which corresponds to the aperture and a signal detected by the processing circuitry in the other irradiation range of the X-rays.

16. The X-ray diagnostic apparatus of claim 15, wherein the processing circuitry executes different types of image processing for data of a range, of an X-ray image generated by the processing circuitry, which corresponds to the aperture and data of another range so as to match an image level of a range, of an X-ray image generated by the processing circuitry, which corresponds to the aperture with an image level of the other range.

17. An X-ray diagnostic apparatus comprising:
an X-ray source configured to generate X-rays;
a plurality of lead plates configured to change a size and position of a first aperture which narrows an irradiation range of X-rays generated from the X-ray source;
an X-ray filter arranged between the X-ray source and the object and including a second aperture, the second aperture including a movable structure; and
processing circuitry configured to:
specify, using a camera, an attention position based on a line of sight of an observer,
detect X-rays transmitted through an object,
generate an X-ray image of the object based on a detection result of X-rays transmitted through the object,
control the plurality of lead plates in accordance with specified attention position of the observer on an X-ray image displayed on a monitor to move a position of the first aperture or change a size of the first aperture,
control the X-ray filter in accordance with specified attention position of the observer on an X-ray image displayed on the monitor to move a position of the second aperture, and
switch between operations of the stop control circuitry and the filter control circuitry in accordance with an instruction from the observer.

18. An X-ray diagnostic apparatus comprising:
a first X-ray source configured to generate X-rays;
a first lead plates configured to change a size and position of the first aperture which narrows an irradiation range of X-rays generated from the first X-ray source;
a second X-ray source configured to generate X-rays;
a second lead plates configured to change a size and position of a second aperture which narrows an irradiation range of X-rays generated from the second X-ray source; and
processing circuitry configured to:
specify, using a camera, an attention position based on a line of sight of an observer,
detect X-rays generated from the first X-ray source,
detect X-rays generated from the second X-ray source, and
control at least one of the first lead plates and the second lead plates in accordance with specified attention position of the observer on a monitor to move the position of at least one of the first aperture and the second aperture or change a size of the aperture.

19. The X-ray diagnostic apparatus of claim 18, wherein the processing circuitry is configured to generate a first X-ray image based on an output from the processing circuitry and generate a second X-ray image based on an output from the processing circuitry,
wherein the processing circuitry decides a size and position of the first aperture and a size and position of the second aperture based on specified attention position of an observer on one of the first X-ray image and the second X-ray image which are displayed on the monitor.

20. The X-ray diagnostic apparatus of claim 18, wherein
the first lead plates includes a plurality of first aperture
  blades configured to change a size, position, and shape
  of the first aperture,
the second lead plates includes a plurality of second
  aperture blades configured to change a size, position,
  and shape of the second aperture,
the processing circuitry is configured to generate a first
  X-ray image based on an output from the processing
  circuitry and generate a second X-ray image based on
  an output from the processing circuitry, and
the processing circuitry decides a size and position of the
  aperture corresponding to one of the first aperture and
  the second aperture and a size, position and shape of the
  aperture corresponding to the other of the first aperture
  and the second aperture based on an attention position
  of an observer on one of the first X-ray image and the
  second X-ray image displayed on the monitor.

* * * * *